US012214018B2

(12) United States Patent
Mahdavi

(10) Patent No.: US 12,214,018 B2
(45) Date of Patent: Feb. 4, 2025

(54) GLUCOSE RESPONSIVE INSULINS

(71) Applicant: PROTOMER TECHNOLOGIES, INC., Pasadena, CA (US)

(72) Inventor: Alborz Mahdavi, Pasadena, CA (US)

(73) Assignee: PROTOMER TECHNOLOGIES, INC., Indianapolis, IN (US)

( * ) Notice: Subject to any disclaimer, the term of this patent is extended or adjusted under 35 U.S.C. 154(b) by 534 days.

(21) Appl. No.: 17/327,498

(22) Filed: May 21, 2021

(65) Prior Publication Data

US 2021/0369815 A1 Dec. 2, 2021

Related U.S. Application Data

(62) Division of application No. 15/571,496, filed as application No. PCT/US2016/031361 on May 6, 2016, now Pat. No. 11,052,133.

(60) Provisional application No. 62/157,897, filed on May 6, 2015.

(51) Int. Cl.
| | | |
|---|---|---|
| *A61K 38/28* | (2006.01) | |
| *A61K 31/70* | (2006.01) | |
| *A61K 38/26* | (2006.01) | |
| *A61K 47/64* | (2017.01) | |
| *A61P 3/10* | (2006.01) | |
| *C07K 14/62* | (2006.01) | |
| *C12N 9/12* | (2006.01) | |
| *A61K 38/00* | (2006.01) | |

(52) U.S. Cl.
CPC .............. *A61K 38/28* (2013.01); *A61K 31/70* (2013.01); *A61K 38/26* (2013.01); *A61K 47/643* (2017.08); *A61P 3/10* (2018.01); *C07K 14/62* (2013.01); *C12N 9/1205* (2013.01); *A61K 38/00* (2013.01); *C07K 2319/00* (2013.01); *C07K 2319/30* (2013.01); *C07K 2319/31* (2013.01); *C12Y 207/01001* (2013.01)

(58) Field of Classification Search
CPC ......... A61K 38/28; A61K 38/26; A61K 38/00
See application file for complete search history.

(56) References Cited

U.S. PATENT DOCUMENTS

| 4,888,414 A | 12/1989 | Knutson |
| 7,316,999 B2 * | 1/2008 | Hoeg-Jensen ......... C07K 14/62 514/6.3 |
| 8,846,624 B2 | 9/2014 | Chaikof et al. |
| 9,867,869 B2 | 1/2018 | Anderson et al. |
| 10,000,571 B2 | 6/2018 | Ashkenazi et al. |
| 10,584,156 B2 | 3/2020 | Weiss |
| 2004/0001827 A1 | 1/2004 | Dennis |
| 2007/0219346 A1 | 9/2007 | Trifiro |
| 2010/0048473 A1 | 2/2010 | Chaikof et al. |
| 2010/0273979 A1 | 10/2010 | Abrahmsen et al. |
| 2010/0278845 A1 | 11/2010 | Heavner |
| 2011/0039769 A1 | 2/2011 | Tagmose et al. |
| 2012/0014908 A1 | 1/2012 | Zion et al. |
| 2012/0135919 A1 | 5/2012 | Lancaster et al. |
| 2013/0028918 A1 | 1/2013 | Song et al. |
| 2014/0037699 A1 | 2/2014 | Zion et al. |
| 2015/0025005 A1 | 1/2015 | Langer et al. |
| 2015/0105317 A1 | 4/2015 | Lin et al. |
| 2016/0082122 A1 | 3/2016 | Bachelet et al. |
| 2020/0325160 A1 | 10/2020 | Kruse et al. |

FOREIGN PATENT DOCUMENTS

| WO | WO 03/048195 A2 | 6/2003 |
| WO | WO 2014/093696 A2 | 6/2014 |
| WO | WO 2017/070617 A1 | 4/2017 |
| WO | WO 2019/092125 A1 | 5/2019 |
| WO | WO 2019/204206 A1 | 10/2019 |
| WO | WO 2020/201041 A2 | 10/2020 |
| WO | WO 2021/022116 A1 | 2/2021 |
| WO | WO 2021/202802 A1 | 10/2021 |

OTHER PUBLICATIONS

Golden et al. ( J. Clin. Endocr. Metab. 94: 1853-1878, 2009).*
Perfetti et al. (Eur. J. Endocr. 143, 717-725, 2000).*
Gutniak et al. ( New England J. Med. 30 326: 1316-1322, 1992).*
Dowlut et al., "An Improved Class of Sugar-Binding Boronic Acids, Soluble and Capable of Complexing Glycosides in Neutral Water," *J. Am. Chem. Soc.* 128, 4226-4227 (2006).
Hoeg-Jensen et al., "Insulins with built-in glucose sensors for glucose responsive insulin release," *Journal of Peptide Science*, vol. 11, pp. 339-346 (2005).
Wu, Xin et al., "Selective sensing of saccharides using simple boronic acids and their aggregates," *Chem. Soc. Rev.*, vol. 42, No. 20, pp. 8032-8048 (2013).
Chu, M.K.L., et al., In vitro and in vivo testing of glucose-responsive insulin-delivery microdevices in diabetic rats, Lab on a Chip, The Royal Society of Chemistry, 2012, pp. 2533-2539.

(Continued)

*Primary Examiner* — Gyan Chandra
(74) *Attorney, Agent, or Firm* — Thomas P. Weber

(57) ABSTRACT

This disclosure provides a composition containing a conjugate with a modified insulin molecule. The conjugate has an insulin molecule, which can be insulin or an insulin analog, glucagon, GLP-1, GLP-2 or a GLP-1 agonist. The conjugate also contains one or more polymers. Each of the one or more polymers is covalently linked to the insulin molecule. Additionally, each of the one or more polymers is covalently linked to between 0 to 50 copies of a decoy ligand, and to between 0 to 50 copies of a glucose-binding agent, such that the combined total number of glucose-binding agents and decoy ligands covalently linked to each of the one or more polymers is at least 1. The conjugate can reversibly bind to soluble glucose and in which the extent of its glucose-binding controls the extent to which the modified insulin is able to bind to and activate the insulin receptor. Methods of making the conjugate, as well as use of the conjugate in treatment, are also provided.

15 Claims, No Drawings

Specification includes a Sequence Listing.

(56) References Cited

OTHER PUBLICATIONS

Ding, Z., et al., Synthesis of glucose-sensitive self-assembled films and their application in controlled drug delivery, Polymer 50, 2009, pp. 4205-4211.
European Search Report issued in corresponding application No. EP16790212.1 dated Sep. 5, 2018, 11 pages.
Menting et al.; "Protective hinge in insulin opens to enable its receptor engagement," Proceedings of the National Academy of Sciences; Aug. 4, 2014; vol. 111; pp. 3395-3404.
Qi, W., Glucose Sensitive Microcapsules from Glutaraldehyde Cross-Linked Hemoglobin and Glucose Oxidase, Biomacromolecules 2009, 10, pp. 1212-1216.
Hoeg-Jensen, Thomas, "Preparation and Screening of Diboronate Arrays for Identification of Carbohydrate Binders," QSAR & Combinatorial Science, vol. 23, No. 5, pp. 344-351 (2004).
Pal, Arnab et al., "Design, Synthesis, and Screening of a Library of Peptidyl Bis(Boroxoles) as Oligosaccharide Receptors in Water: Identification of a Receptor for the Tumor Marker TF-Antigen Disaccharide," Angewandte Chemie International Edition, vol. 49, No. 8, pp. 1492-1495 (2010).
Tan, Lei et al., "Glucose- and pH-Responsive Nanogated Ensemble Based on Polymeric Network Capped Mesoporous Silica," Applied Materials & Interfaces, vol. 7, No. 11, pp. 6310-6316 (2015).
International Search Report for International Application No. PCT/US2021/025261, dated Jul. 1, 2021 (6 pages).
International Search Report of International Application No. PCT/US2021/059802, mail date Mar. 9, 2022 (7 pages).

\* cited by examiner

GLUCOSE RESPONSIVE INSULINS

CROSS REFERENCE TO RELATED APPLICATIONS

This application is a divisional of U.S. patent application Ser. No. 15/571,496, filed on Nov. 2, 2017, now U.S. Pat. No. 11,052,133, which is a National Phase patent application of and claims priority to and the benefit of International Patent Application Number PCT/US2016/031361, filed on May 6, 2016, which claims priority to and the benefit of U.S. Provisional Patent Application No. 62/157,897, filed on May 6, 2015. The entire contents of all of which are incorporated herein by reference.

SEQUENCE LISTING

The present application includes a Sequence Listing in electronic format. The Sequence Listing is provided as a file titled "206816SEQLISTING," amended Apr. 25, 2019, being 42,033 bytes in size. The information in the electronic format of the Sequence Listing is incorporated herein by reference in its entirety.

BACKGROUND

Previous strategies for development of glucose responsive insulins (GRIs) have generally included controlled-release insulin delivery systems in which insulin is released in response to excess glucose levels in the blood. Prior insulin delivery approaches include vesicles, gels or networks consisting of peptides or proteins, including glucose oxidase, or lectins including concanavalin A. In addition, modified insulins that can non-covalently bind to albumin or diols in the body and be released upon binding to glucose have been used. Lectin-based materials that can bind to glucose have also been described, but these materials rely on release of amounts of insulin in response to desired concentrations of glucose. These approaches include systems that rely on release of conjugates in response to glucose, including lectin-based systems and albumin binding insulin analogues. In general, such previously reported approaches are not necessarily reversible because once insulin is released in response to glucose, it can be diluted in a solution containing glucose and not necessarily captured back if insulin levels decrease. As such, reversibility is not easily achieved. In certain previously reported cases, lectins are used to achieve specificity towards glucose; however, the use of lectins may cause an immune reaction or be mitogenic, in which case additional modifications must be made to lectins to circumvent such limitations.

Some of these and other previously described GRIs include an affinity ligand and glucose binding receptor, the latter of which is connected to the B-chain of the insulin molecule in conjunction with a single affinity ligand connected to the A-chain of the insulin molecule, which may limit the ability of such a GM to have graded, proportionate and specific response to changes in glucose levels, particularly in the 1-20 mM glucose range. At such high glucose concentrations, a multiplicity of interactions may be required between a glucose-binding receptor and more than one ligand to achieve a graded response to glucose. The A-chain and B-chain of insulin cannot accommodate large macromolecular frameworks (owing to the requirement to engage the insulin receptor for activity) and yet at the same time macromolecular frameworks need to be in close proximity to insulin in order to control its activity. As such, there is a need to develop GRIs that can bind to the insulin receptor and be proportionately responsive to different glucose concentrations and provide a graded and reversible response to changes in glucose levels under physiological conditions.

SUMMARY

The present invention is directed, in part, to a conjugate satisfies the need of binding to the insulin receptor and be proportionately responsive to different glucose concentrations, as well as provide a graded and reversible response to changes in glucose levels under physiological conditions. In one embodiment, a conjugate comprises an insulin molecule, decoy ligand, glucose-binding agent, and one or more polymers. At least one of the one or more polymers is covalently linked to the insulin molecule, covalently linked to between 0 to 50 copies of the decoy ligand, and covalently linked to between 0 to 50 copies of a glucose-binding agent, such that the combined total number of glucose-binding agents and decoy ligands covalently linked to each of the one or more polymers is at least 1. The insulin molecule can be, for example, insulin, or an insulin analog, glucagon, GLP-1, GLP-2 or a GLP-1 agonist.

In another embodiment, at least one of the one or more polymers is covalently linked to a second polymer, and the second polymer is covalently linked to between 0 to 50 copies of the decoy ligands and between 0 to 50 copies of the glucose-binding agents such that the combined total number of glucose-binding agents and decoy ligands covalently linked to the second polymers is at least 1. The at least one of the one or more polymers can be a polypeptide having no more than 1000 amino acids. The at least one of the one or more polymers can be covalently linked to an albumin molecule, an immunoglobulin, and/or an immunoglobulin fragment.

In one embodiment, the insulin molecule has an A-chain and a B-chain. The B-chain of the insulin molecule can be covalently linked to the A-chain of the insulin molecule through a contiguous polypeptide chain. In another embodiment, at least one of the one or more polymers can be covalently linked to the A-chain of the insulin molecule. In an additional embodiment, at least one of the one or more polymers can be covalently linked to the N-terminus and/or the C-terminus of the A-chain of the insulin molecule. In another embodiment, at least one of the one or more polymers can be covalently linked to the B-chain of the insulin molecule such as, for example, covalently linked with a peptide bond. In an additional embodiment, at least one of the one or more polymers can be covalently linked to the N-terminus and/or the C-terminus of the B-chain of the insulin molecule. In an additional embodiment, the at least one of the one or more polymers can be covalently linked to both the A-chain and the B-chain of the insulin molecule.

In one embodiment, at physiological conditions and pH, the conformation of the insulin molecule can be restricted so that residues Tyr26 to the C-terminus of the B-chain are no more than 15 angstroms apart from the N-terminus of the A-chain for at least 10% of time in solutions where the majority of the glucose-binding agents are bound to the decoy ligands. In another embodiment, at physiological conditions and pH, the conformation of the insulin molecule can be restricted so that residues Gly23 on the B-chain and Cys20 on the A-chain are no more than 10 angstroms apart for at least 10% of the time in solutions where the majority of the glucose-binding agents are bound to the decoy ligands.

In another embodiment, at physiological conditions and pH, the conformation of the insulin molecule can be restricted so that residues Gly23 on the B-chain and Cys20 on the A-chain are no more than 6.5 angstroms apart for at least 10% of the time in solutions wherein the majority of the glucose-binding agents are bound to the decoy ligands. In an additional embodiment, at physiological conditions and pH, the conformation of the insulin molecule can be restricted so that residues Gly23 on the B-chain and Cys20 on the A-chain are no more than 10 angstroms apart for at least 10% of the time in solutions with less than 6 mM glucose. In another embodiment, at physiological conditions and pH, the conformation of the insulin molecule is restricted so that residues Gly23 on the B-chain and Cys20 on the A-chain are no more than 10 angstroms apart for at least 10% of the time in solutions with less than 4.5 mM glucose.

In one embodiment, the glucose-binding agents can bind to the decoy ligands in the absence of soluble glucose. In another embodiment, the glucose-binding agents can reversibly bind to the decoy ligands with a dissociation constant between 10 pM and 20 mM.

In another embodiment, the decoy ligands can bind to the glucose-binding agents in the absence of soluble glucose, and the decoy ligands can bind to the glucose-binding agents with a lower affinity in the presence of glucose or when the glucose-binding agent is bound to glucose. In another embodiment, the glucose-binding agents cannot bind a glucose and a decoy ligand simultaneously. Additionally, the decoy ligands can contain a saccharide or derivatives thereof an inositol, or isomers of myo-inositol, or derivatives thereof or a sugar alcohol, and/or a covalently connected glucose conjugate.

In one embodiment, the decoy ligands can each independently have a valency of between 1 and 10. In another embodiment, the glucose-binding agents can each independently have a valency of between 1 and 10. Additionally, at least one of the glucose-binding agents can non-covalently bind to the insulin molecule.

In one embodiment, at least one of the one or more polymers can be a polypeptide, and can have the sequence of human albumin, SEQ ID NO: 18, SEQ ID NO: 19, and/or SEQ ID NO: 20.

In another embodiment, at least one of the one or more polymers can be covalently conjugated to, or has within its sequence, one or more copies of the peptide sequence consisting of amino acids Z1-Z17 where Z1 is K, T, C, acyl group at N-terminus of Z2 or absent, Z2 is V or D, Z3 is E or I, Z4 is E, G or C, Z5 is A, L or V, Z6 is S, P, H, E, Q or N, Z7 is R, S or A, Z8 is W or L, Z9 is G, T, I or K, Z10 is G or L, Z11 is H or absent, Z12 is I or absent, Z13 is L or absent, Z14 is A or absent, Z15 is A or absent, Z16 is L or absent, and Z17 is P or absent. Additionally, at least one of the one or more polymers can have at least one boronte or phenylboronic acid group.

In another embodiment, at least one of the one or more of the glucose-binding agents can be in-part boronate functionalized, a hexokinase, and/or a modified hexokinase, In one embodiment, the one or more polymers can be connected to hexokinase or a modified hexokinase including hexokinase IV or glucokinase.

In another embodiment, the insulin molecule can be covalently conjugated at two sites to hexokinase or glucokinase, or to a protein with at least 10% amino acid sequence similarity to the human hexokinase or glucokinase.

In one embodiment, at least one of the one or more polymers can have amino acids selected independently as a subset from the set of amino acids E, G, K, S, C and/or at least one artificial amino acid. In another embodiment, the insulin contains at least one artificial amino acid.

In another embodiment, the insulin can have at least one artificial amino acid which has a side chain with a terminal azide group that has been linked by click chemistry reaction to one of the one or more polymers.

In another embodiment, the insulin can have at least one artificial amino acid which has a side chain with a terminal alkyne group that has been linked by click chemistry reaction to one of the one or more polymers.

In one embodiment, at least one of the one or more polymers can have at least one repeat of the amino acid sequence of SEQ ID NO: 8 wherein X is any amino acid, including an artificial amino acid.

In another embodiment, one or more of the decoy ligands can independently contain a chemical structure described by formula F1 or formula F2:

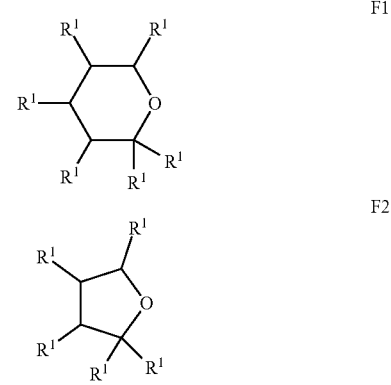

wherein:
each $R^1$ can independently have (R) or (S) stereochemistry and is independently selected from —H, —$OR^3$, —$N(R^3)_2$, —$SR^3$, —OH, —$OCH_3$, —$OR^5$, —$R^6$—$R^7$, —NHC(O)$CH_3$, —$CH_2R^3$, —NHC(O)$CH_3$, —$CH_2OH$, —$CH_2OR^5$, —$NH_2$ or —$CH_2R^4$ each $R^2$ can be independently selected from —H or an optionally substituted group selected from $C_{1-6}$ aliphatic, phenyl, a 5-6 membered monocyclic heteroaryl ring having 1-4 heteroatoms selected from nitrogen, oxygen, or sulfur, or a 4-7 membered heterocyclic ring having 1-2 heteroatoms selected from nitrogen, oxygen, or sulfur each $R^3$ can be independently selected from —H, acetyl, phosphate, —$R^2$, —$SO_2R^2$, —$S(O)R^2$, —$P(O)(OR^2)_2$, —$C(O)R^2$, —$CO_2R^2$, or —$C(O)N(R^2)_2$ each $R^4$ can be independently selected from —H, —OH, —$OR^3$, —$N(R^3)_2$, —$OR^5$ or $SR^3$;

each $R^5$ can be independently selected from either a mono- di- or tri-saccharide, a pentose or a hexose each $R^6$ can be independently selected from a linker, —$NCOCH_2$—, —$OCH_2CH_2$—, O—$C_{1-9}$ alkylene, a substituted $C_{1-9}$ alkylene in which one or more methylene is optionally replaced by —O—, —$CH_2$—, —$OCH_2$—, —$N(R^2)C(O)$—, —$N(R^2)C(O)N(R^2)$—, —$SO_2$—, —$SO_2N(R^2)$—, —$N(R^2)SO_2$—, —S—, —$N(R^2)$—, —C(O)—, —OC(O)—, —C(O)O—, —$C(O)N(R^2)$—, or —$N(R^2)SO_2N(R^2)$— each $R^7$ can be independently selected from —$N(R^2)_2$, —F, —Cl, —Br, —I, —SH, —$OR^2$, —$SR^2$, —$NH_2$, —$N_3$, —C≡C$R^2$, —$CH_2$C≡CH, —$CO_2R^2$, —C(O)$R^2$, or —$OSO_2R^2$. —$N(R^2)_2$, —$OR^2$, —$SR^2$ or —$CH_2NH_2$ In one embodiment, one or more of the glucose-binding agents can independently contain a chemical structure described by formula F3 or formula F4:

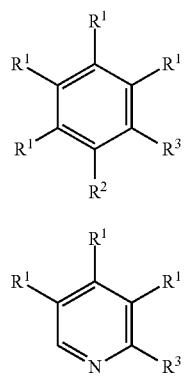

F3

F4 wherein:
each $R^1$ can be independently selected from —H, —F, —Cl, —$CH_3$, —B(OH)$_2$, —C≡N, —$NO_2$, or —$R^4$
each $R^2$ can be independently selected from —H, —C≡N, —$(SO_2)NH(R^4)$, or —$R^4$
each $R^3$ can be independently selected from —C≡N, —CONH($R^4$), —NH($R^4$), ($SO_2$)NH($R^4$), or —$R^4$
each $R^4$ can be independently selected from —H, —$N_3$, —C≡CH, —$CH_2N(R^5)$ or a linker
each $R^5$ can be independently selected from —H or a linker.

In one embodiment, at least one of the one or more polymers can be conjugated to a recombinant protein of human origin.

In one embodiment, there is described a conjugate having a glucagon molecule. The glucagon molecule can be glucagon, GLP-1, GLP-2 or a GLP-1 agonist. The conjugate can also have one or more polymers, wherein each of the one or more polymers is covalently linked to the glucagon molecule, wherein each of the one or more polymers is covalently linked to between 0 to 50 copies of a decoy ligand, and wherein each of the one or more polymers is covalently linked to between 0 to 50 copies of a glucose-binding agent, such that the combined total number of glucose-binding agents and decoy ligands covalently linked to each of the one or more polymers is at least 1.

In one embodiment, a method of administering the composition of claim 1 to a patient in need thereof is described, The patient can be a mammal such as, for example, a human.

In one embodiment, a method of making the conjugate is described, in which at least one of the glucose-binding agents and at least one of the decoy ligands can be first non-covalently linked together in solution and then covalently linked to at least one of the one or more polymers while the one or more polymer is already covalently connected to insulin molecule and while the insulin molecule is non-covalently bound to a biomolecule, which can be removed thereafter.

DETAILED DESCRIPTION

Unless specifically described herein, chemical terms, functional groups, and general terms used throughout the specification are identified in accordance with the Periodic Table of the Elements, CAS version, Handbook of Chemistry and Physics, 75[th]Ed., inside cover. Specific functional groups are given their meaning as described by general principles of organic chemistry, as well as specific functional moieties and reactivity, as described in Organic Chemistry, Thomas Sorrell, University Science Books, Sausalito, 1999; Larock, Comprehensive Organic Transformations, VCH Publishers, Inc., New York, 1989; Carruthers, Some Modern Methods of Organic Synthesis, 3rd Edition, Cambridge University Press, Cambridge, 1987; Smith and March, March's Advanced Organic Chemistry, 5th Edition, John Wiley & Sons, Inc., New York, 2001.

The terms "a," "an," and "the" and similar referents used herein are to be construed to cover both the singular and the plural unless their usage in context indicates otherwise.

As used herein, the terms "insulin" or "insulin molecule" encompasses both wild-type and modified forms of functional insulin. In this context, "functional" means capable of binding to and activating the insulin receptor, or capable of causing a measurable reduction in blood glucose when administered in vivo. Insulin includes insulin from any species whether in purified, synthetic or recombinant form and includes human insulin, porcine insulin, bovine insulin, sheep insulin and rabbit insulin. A variety of altered forms of insulin are known in the art and may be chemically altered such as by addition of a chemical moiety such as a PEG group or a fatty acyl chain. Altered insulins may be mutated including additions, deletions or substitutions of amino acids. The term "desB30" refers to an insulin lacking the B30 amino acid residue.

As used herein, the term "percentage homology" refers to the percentage of sequence identity between two sequences after optimal alignment; identical sequences have a percentage homology of 100%. Optimal alignment may be performed by homology alignment algorithm described by the search for similarity method of Pearson and Lipman, *Proc. Natl. Acad. Sci. USA* 85:2444 (1988), by general method described for search for similarities by Neddleman and Wunsch, *J. Mol. Biol.* 48:443 (1970), including implementation of these algorithms or visual comparison.

As used herein, the terms "linker" or "chemical linker" describes any type of covalent chemical linkage that is used to connect two molecules together, where molecules in this context are sometimes referred to as "units" herein. This includes cases where the units are different molecules, such as a polymer with insulin; a polymer with a protein; a polymer with a decoy ligand; a polymer with a glucose-binding agent; any subsection of a polymer with the remaining section of a polymer. "Conjugate" refers to any two molecules that are covalently connected by a linker. Two molecules can be connected together at one point through one linker and such covalently connected components are linked. In some embodiments of the invention in which the polymer has more than one segment, these segments can be linked using linkers. In certain embodiments such polymer sections may be more than two, and it is to be understood that a combination of different linkers may be used within the same conjugates of units. In certain embodiments, the same conjugates resulting in a given modified insulin may have more than one decoy ligand or more than one glucose-binding agent or more than one protein which is covalently connected to the polymer, and it is to be understood that in certain embodiments the chemical linkers used for each one of these covalent linkages may be different for each copy of a given unit. The units may be covalently connected through any number of chemical bonds as generally described in Bioconjugate Techniques (Third edition), edited by Greg T.

Hermanson, Academic Press, Boston, 2013. In certain embodiments, units can be covalently connected or linked through an amide, ester, ether, thioether, isourea, imine, triazole or any previously reported covalent conjugation chemistry that can be used to covalently connect one peptide or protein or synthetic polymer to a second peptide or protein or synthetic polymer. In certain embodiments two components may be linked using "click chemistry" reactions as is known in the art. These include, for example, cycloaddition reactions including but not limited to 3+2 cycloadditions, Strain-promoted Alkyne-Nitrone Cycloaddition, Reactions of Strained Alkenes, Alkene and Tetrazine inverse-demand Diels-Alder, Copper(I)-Catalyzed Azide-Alkyne Cycloaddition (CuAAC), Strain-promoted Azide-Alkyne Cycloaddition, Staudinger ligation, nucleophilic ring-opening reaction, and additions to carbon-carbon multiple bonds. Some of these reactions are described for example by H. C. Kolb, M. G. Finn and K. B. Sharpless (2001); Click Chemistry: Diverse Chemical Function from a Few Good Reactions, Angewandte Chemie International Edition 40 (11): 2004-2021; Kolb and Sharpless, *Drug Discovery Today* 8:1128-1137, 2003; Huisgen, R. Angew. Chem. Int. Ed. Engl. 1963, 2, 565; Agard, N. J.; Baskin, J. M.; Prescher, J. A.; Lo, A.; Bertozzi, C. R. ACS Chem. Biol. 2006, 1, 644. One skilled in the art will recognize that it is important to use judicious choice of buffers, pH and reaction conditions for such click reactions. For example, the use of chelators such as EDTA is to be avoided for CuAAC reaction. In some embodiments the linker is the result of a "bioorthogonal reaction" as is known in the art. Such reactions are for example described by Sletten, Ellen M.; Bertozzi, Carolyn R. (2009). Bioorthogonal Chemistry: Fishing for Selectivity in a Sea of Functionality, Angewandte Chemie International Edition 48 (38): 6974-98; Prescher, Jennifer A; Bertozzi, Carolyn R (2005). Chemistry in living systems, Nature Chemical Biology 1 (1): 13-21. In certain embodiments, units may be linked using native chemical ligation as described for example by Dawson, P. E.; Muir, T. W.; Clark-Lewis, I.; Kent, S. B. (1994) Synthesis of proteins by native chemical ligation, Science 266 (5186): 776-778.

In certain embodiments of the invention, different units are connected together through a peptide bond, wherein the peptide bond is the linker. For example, if the end of a polymer contains a peptide with an N-terminus that is connected through a peptide bond to the C-terminus of the B-chain of insulin, then this forms a continuous polypeptide in which the linker is a peptide bond. Alternatively, in certain embodiments, side chains of amino acids are used for covalent linkage, in which case the side chain of the amino acid comprises part of the linker. In general, it is to be understood that the first and second members of a pair of reactive groups (for example, a carboxyl group and an amine group which react to produce an amide bond) can be present on either one of the units being linked.

An "insulin A-chain" is the chain of insulin that has the highest percentage homology to the A-chain of wild-type human insulin.

An "insulin B-chain" is the chain of insulin that has the highest percentage homology to the B-chain of wild-type human insulin.

As used herein, the terms "covalently connected," "covalently conjugated," or "through a covalent conjugation" refers to a chemical linkage.

The term "albumin" means human serum albumin or a protein with at least 60% percentage homology to human serum albumin protein. It is to be understood that in certain embodiments the albumin may be further chemically modified for the purposes of conjugation. Such modifications may include a covalently connected linker. The amino sequence of the human serum albumin is: MKWVTFISLL FLFSSAYSRG VFRRDAHKSE VAHRFKDLGE ENFKA-LVLIA FAQYLQQCPF EDHVKLVNEV TEFAKTCVAD ESAENCDKSL HTLFGDKLCT VATLRETYGE MADC-CAKQEP ERNECFLQHK DDNPNLPRLV RPE-VDVMCTA FHDNEETFLK KYLYEIARRH PYFY-APELLF FAKRYKAAFT ECCQAADKAA CLLPKLDELR DEGKASSAKQ RLKCASLQKF GER-AFKAWAV ARLSQRFPKA EFAEVSKLVT DLTKVHTECC HGDLLECADD RADLAKYICE NQD-SISSKLK ECCEKPLLEK SHCIAEVEND EMPADLPSLA ADFVESKDVC KNYAEAKDVF LGMFLYEYAR RHPDYSVVLL LRLAKTYETT LEKCCAAADP HECYA-KVFDE FKPLVEEPQN LIKQNCELFE QLGEYKFQNA LLVRYTKKVP QVSTPTLVEV SRNLGKVGSK CCK-HPEAKRM PCAEDYLSVV LNQLCVLHEK TPVS-DRVTKC CTESLVNRRP CFSALEVDET YVPKEFNAET FTFHADICTL SEKERQIKKQ TALVELVKHK PKATKEQLKA VMDDFAAFVE KCCKADDKET CFAEEGKKLV AASQAALGL (SEQ ID NO:1) where the first 24 amino acids may be removed.

The term "valency" refers to the number of binding units on a ligand that are able to bind to a receptor. A monovalent ligand, receptor, glucose-binding agent or decoy ligand has 1 binding site and has a valency of 1. A divalent ligand, receptor, glucose-binding agent or decoy ligand has two binding sites, and has a valency of 2. A polyvalent ligand, receptor, glucose-binding unit or decoy ligand has 3-10 binding sites and has a valency of 3-10, respectively.

As used herein, the term "peptide" or "protein" means two or more amino acids linked by peptide bonds.

The term "decoy ligand" refers to a molecule to which a glucose-binding agent can bind.

The term "glucose-binding agent" includes molecules that can bind to glucose. In certain embodiments the glucose-binding agent can also bind to molecules other than glucose. In one embodiment, the glucose-binding agent can include the active site of a glucose-binding protein or a glucose-binding proteins in its entirety.

A "glucose conjugate" herein is any linked molecule with formula F1 or F2 or any linked glucose or saccharide.

The term "CAS #" as used herein is also referred to as CASRN or CAS Number, is a unique numerical identifier assigned by Chemical Abstracts Service (CAS) to every chemical substance described in the open scientific literature.

A "lectin" is a protein that binds with specificity to saccharides and polysaccharides.

The term "polymer" refers to a structure that includes a contiguous string of covalently connected monomers, with at least two connected monomers and wherein such monomers may be different or the same. A polymer may be linear or branched. This term includes copolymers, block-copolymers in which different types of monomer are grouped separately within the same polymer. A polymer includes but is not limited to, proteins, polypeptides and synthetic polymers.

A "synthetic polymer" is polymer that can be chemically synthesized and does not directly come from a biological origin or monomers made by biological organisms.

By "at physiological conditions and pH" it is meant that conditions that would normally be present in the blood of a healthy adult human.

By "biomolecule" it is meant a molecule of biological origin. Such a molecule may include a protein with certain specific folds or amino acid sequence or DNA or RNA.

As used herein, a "polypeptide" is a polymer in which the monomers are covalently linked together through peptide bonds. Polypeptides include polymers consisting of amino acids, including any L or D amino acid, derived from a natural or non-natural set of amino acids and any analogs that are known in the art or otherwise described herein. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

"Conservative substitution" means the replacement of a first amino acid residue with a second amino acid residue where the second amino acid residue does not substantially affect the advantageous properties of the substance. Such substitutions are well known in the art and include substituting a tryptophan, leucine or isoleucine for a phenylalanine, substituting a valine for a methionine and substituting a glutamate for an aspartate.

As used in this disclosure, the term "comprise" and variations of the term, such as "comprising" and "comprises," are not intended to exclude other additives, components, integers ingredients or steps.

The term "mammal" is defined as an individual belonging to the class Mammalia and includes, without limitation, humans, domestic and farm animals, and zoo, sports, and pet animals, such as sheep, dogs, horses, cats and cows.

A "therapeutic composition" as used herein means a substance that is intended to have a therapeutic effect such as pharmaceutical compositions, genetic materials, biologics, and other substances. Pharmaceutical compositions may be configured to function in inside the body with therapeutic qualities, concentration to reduce the frequency of replenishment, and the like.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by ordinary medical practitioner, and may vary depending on factors known in the art, such as, e.g. the type of disease, the patient's history and age, the stage of disease, and the administration of other therapeutic agents.

The invention includes a modified insulin, or conjugate, that can reversibly bind to soluble glucose. The extent of glucose-binding controls the extent to which the modified insulin is able to bind to and activate the insulin receptor. It is contemplated that a graded response to different concentrations of soluble glucose is provided through interactions between multiple glucose-binding agents and decoy ligands. The extent of binding of the glucose-binding agents to decoy ligands or segments of the modified insulin restrict or relax the conformation of the modified insulin and thereby control the extent to which the modified insulin binds the insulin receptor. In one embodiment, there is a chain conformation change within insulin itself, for example within the B-chain of insulin which acts to control the movement of the C-terminal end of the B-chain of insulin and can be used to control the extent to which insulin can bind to and activate the insulin receptor. The chain conformation change can occur within chains that are covalently connected to insulin and results in movement of insulin, either closer to or further away from, a second macromolecule which hinders binding of insulin to the insulin receptor under physiological conditions. It is contemplated that the modified insulins described herein can bind to glucose, or are capable of sensing glucose, and can change from an inactive to an active form or configuration in response to glucose. The active form or configuration is a form or configuration that is able to bind and activate the insulin receptor. In certain uses modified insulins described herein may be delivered to the body by injection, or by other routes and can reversibly bind to soluble glucose in a non-depot form. In certain embodiment modified insulins described herein can additionally be released over an extended period of time from a local depot in the body.

Insulin and Modified Insulin

Insulin is an important regulator of blood glucose levels. In a normal individual, insulin is present and when released by the pancreas it acts to reduce blood sugar levels. Diabetes mellitus (DM), commonly referred to as diabetes, is a group of metabolic diseases in which there are high blood sugar levels over a prolonged period.

Modified insulin describes insulin that is chemically altered as compared to wild type insulin, such as, but not limited to, by addition of a chemical moiety such as a PEG group or a fatty acyl chain. Altered insulins may be mutated including additions, deletions or substitutions of amino acids. Different protomers of insulin may result from these changes and be incorporated into certain embodiments.

Generally active forms of insulins have less than 11 such modifications (e.g., 1-4, 1-3, 1-9, 1-8, 1-7, 1-6, 2-6, 2-5, 2-4, 1-5, 1-2, 2-9, 2-8, 2-7, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1). The wild-type sequence of human insulin (A-chain and B-chain), has an A-chain with the amino acid sequence GIVEQCCTSICSLYQLENYCN (SEQ ID NO:2), and a B-chain having the amino acid sequence FVNQHLCGSHLVEALYLVCGERGFFYTPKT (SEQ ID NO:3).

Human insulin differs from rabbit, porcine, bovine, and sheep insulin in amino acids A8, A9, A10, and B30 which are in order the following: Thr, Ser, Ile, Thr for human; Thr, Ser, Ile, Ser for rabbit; Thr, Ser, Ile, Ala for porcine; Ala, Gly, Val, Ala for sheep; and Ala, Ser, Val, Ala for bovine. A modified insulin may in various embodiments include an insulin which is mutated at the B28 or the B29, or B28 and B29 positions of the B-chain. For example, insulin lispro is a fast acting modified insulin in which the penultimate lysine and proline residues on the C-terminal end of the B-chain have been reversed. Insulin aspart is a fast-acting modified insulin in which proline has been substituted with aspartic acid at position B28. It is contemplated in some embodiments of the invention that mutations at B28 and B29 may come with additional mutations. Insulin glulisine is a fast-acting modified insulin in which aspartic acid has been replaced by a lysine residue at position B3, as well as the replacement of lysine with a glutamic acid residue at position B29.

In certain embodiments the isoelectric point of insulins herein may be shifted relative to wild-type human insulin by addition or substitution of amino acids or otherwise achieved through chemical modification. For example, insulin glargine is a basal insulin in which two arginine residues have been added to the C-terminus of the B-peptide and A21 has been replaced by glycine. The insulin may not have one or more of the residues B1, B2, B3, B26, B27, B28, B29, B30. In some embodiments, the insulin molecule contains additional amino acid residues on the N- or C-terminus of the A-chain or B-chain. In some embodiments, one or more amino acid residues are located at positions A0, A21, B0 and/or B31 or are missing. In certain embodiments, an insulin molecule of the present disclosure is mutated such that one or more amino acids are replaced with acidic forms. By way of example, an asparagine may be replaced with aspartic acid or glutamic acid, similarly glutamine may be replaced with aspartic acid or glutamic acid. In certain embodiments A21 may be an aspartic acid, B3 may be an aspartic acid, or both positions may contain an aspartic acid. One skilled in the art will recognize that it is possible to make any previously reported, or widely accepted mutations or modifications to insulin that retains biological activity, and that the modified insulin can be used in the invention. In certain embodiments, an insulin may be linked at any position to a fatty acid, or acylated with a fatty acid at any amino group, including those on side chain of lysines or alpha-amino group on the N-terminus of insulin and the fatty acid may include C8, C9, C10, C11, C12, C14, C15, C16, C17, C18. In some embodiments, the fatty acid chain is 8-20 carbons long. By way of example, such modifications can resemble those in insulin detemir in which a myristic acid is covalently conjugated to lysine at B29 and B30 is deleted or absent. In certain embodiments, position B28 of the insulin molecule is lysine and the epsilon(ε)-amino group of this lysine is conjugated to a fatty acid.

In certain embodiments, a modified insulin molecule of the present disclosure comprises the mutations and/or chemical modifications including, but not limited to one of the following insulin molecules: $N^{\epsilon B29}$-octanoyl-$Arg^{B0}Gly^{A21}Asp^{B3}Arg^{B31}Arg^{B32}$-HI, $N^{\epsilon B29}$-octanoyl-$Arg^{B31}Arg^{B32}$-HI, $N^{\epsilon B29}$-octanoyl-$Arg^{A0}Arg^{B31}Arg^{B32}$-HI, $N^{\epsilon B28}$-myristoyl-$Gly^{A21}Lys^{B28}Pro^{B29}Arg^{B31}Arg^{B32}$-HI, $N^{\epsilon B28}$-myristoyl-$Gly^{A21}Gln^{B3}Lys^{B28}Pro^{B30}Arg^{B31}Arg^{B32}$-HI, $N^{\epsilon B28}$-myristoyl-$Arg^{A0}Gly^{A21}Lys^{B28}Pro^{B29}Arg^{B31}Arg^{B32}$-HI, $N^{\epsilon B28}$-myristoyl-$Arg^{A0}Gly^{A21}Gln^{B3}Lys^{B28}Pro^{B29}Arg^{B31}Arg^{B32}$-HI, $N^{\epsilon B28}$-myristoyl-$Arg^{A0}Gly^{A21}Asp^{B3}Lys^{B28}Pro^{B29}Arg^{B31}Arg^{B32}$-HI, $N^{\epsilon B28}$-myristoyl-$Lys^{B28}Pro^{B29}Arg^{B31}Arg^{B32}$-HI, $N^{\epsilon B28}$-myristoyl-$Arg^{A0}Lys^{B28}Pro^{B29}Arg^{B31}Arg^{B32}$-HI, $N^{\epsilon B28}$-octanoyl-$Gly^{A21}Lys^{B28}Pro^{B29}Arg^{B31}Arg^{B32}$-HI, $N^{\epsilon B28}$-octanoyl-$Gly^{A21}Gln^{B3}Lys^{B28}Pro^{B29}Arg^{B31}Arg^{B32}$-HI, $N^{\epsilon B28}$-octanoyl-$Arg^{A0}Gly^{A21}Lys^{B28}Pro^{B29}Arg^{B31}Arg^{B32}$-HI, $N^{\epsilon B29}$-palmitoyl-HI, $N^{\epsilon B29}$-myrisotyl-HI, $N^{\epsilon B28}$-palmitoyl-$Lys^{B28}Pro^{B29}$-HI, $N^{\epsilon B28}$-myristoyl-$Lys^{B28}Pro^{B29}$-HI, $N^{\epsilon B29}$-palmitoyl-des(B30)-HI, $N^{\epsilon B30}$-myristoyl-$Thr^{B29}Lys^{B30}$-HI, $N^{\epsilon B30}$-palmitoyl-$Thr^{B29}Lys^{B30}$-HI, $N^{\epsilon B29}$-(N-palmitoyl-γ-glutamyl)-des(B30)-HI, $N^{\epsilon B29}$-(N-lithocolyl-γ-glutamyl)-des(B30)-HI, $N^{\epsilon B29}$-(co-carboxyheptadecanoyl)-des(B30)-HI, $N^{\epsilon B29}$-(ω-carboxyheptadecanoyl)-HI, $N^{\epsilon B29}$-octanoyl-HI, $N^{\epsilon B29}$-myristoyl-$Gly^{A21}Arg^{B31}Arg^{B31}$-HI, $N^{\epsilon B29}$-myristoyl-$Gly^{A21}Gln^{B3}Arg^{B31}Arg^{B32}$-HI, $N^{\epsilon B29}$-myristoyl-$Arg^{A0}Gly^{A21}Arg^{B31}Arg^{B32}$-HI, $N^{\epsilon B29}$-$Arg^{A0}Gly^{A21}Gln^{B3}Arg^{B31}Arg^{B32}$-HI, $N^{\epsilon B29}$-myristoyl-$Arg^{A0}Gly^{A21}Asp^{B3}Arg^{B31}Arg^{B32}$-HI, $N^{\epsilon B29}$-myristoyl-$Arg^{B31}Arg^{B32}$-HI, $N^{\epsilon B29}$-myristoyl-$Arg^{A0}Arg^{B31}Arg^{B32}$-HI, $N^{\epsilon B29}$-octanoyl-$Gly^{A21}Arg^{B31}Arg^{B32}$-HI, $N^{\epsilon B29}$-octanoyl-$Gly^{A21}Gln^{B3}Arg^{B31}Arg^{B32}$-HI, $N^{\epsilon B29}$-octanoyl-$Arg^{A0}Gly^{A21}Arg^{B31}Arg^{B32}$-HI, $N^{\epsilon B29}$-octanoyl-$Arg^{A0}Gly^{A21}Gln^{B3}Arg^{B31}Arg^{B32}$-HI, $N^{\epsilon B28}$-octanoyl-$Arg^{A0}Gly^{A21}Gln^{B3}Lys^{B28}Pro^{B29}Arg^{B31}Arg^{B32}$-HI, $N^{\epsilon B28}$-octanoyl-$Arg^{A0}Gly^{A21}Asp^{B3}Lys^{B28}Pro^{B29}Arg^{B31}Arg^{B32}$-HI, $N^{\epsilon B28}$-octanoyl-$Lys^{B28}Pro^{B29}Arg^{B31}Arg^{B32}$-HI, $N^{\epsilon B28}$-octanoyl-$Arg^{A0}Lys^{B28}Pro^{B29}Arg^{B31}Arg^{B32}$-HI. $N^{\epsilon B29}$-pentanoyl-$Gly^{A21}Arg^{B31}Arg^{B32}$-HI, $N^{\alpha B1}$-hexanoyl-$Gly^{A21}Arg^{B31}Arg^{B32}$-HI, $N^{\alpha A1}$-heptanoyl-$Gly^{A21}Arg^{B31}Arg^{B32}$-HI, $N^{\epsilon B29}$-octanoyl-$N^{\alpha B1}$-octanoyl-$Gly^{A21}Arg^{B31}Arg^{B32}$-HI, $N^{\epsilon B29}$-propionyl-$N^{\alpha A1}$-propionyl-$Gly^{A21}Arg^{B31}Arg^{B32}$-HI, $N^{\alpha A1}$-acetyl-$N^{\alpha B1}$-acetyl-$Gly^{A21}Arg^{B31}Arg^{B32}$-HI, $N^{\epsilon B29}$-formyl-$N^{\alpha A1}$-formyl-$N^{\alpha B1}$-formyl-$Gly^{A21}Arg^{B31}Arg^{B32}$-HI, $N^{\epsilon B29}$-formyl-des(B26)-HI, $N^{\alpha B1}$-acetyl-$Asp^{B28}$-HI, $N^{\epsilon B29}$-propionyl-$N^{\alpha A1}$-propionyl-$N^{\alpha B1}$-propionyl-$Asp^{B1}Asp^{B3}Asp^{B21}$-HI, $N^{\epsilon B29}$-pentanoyl-$Gly^{A21}$-HI, $N^{\alpha B1}$-hexanoyl-$Gly^{A21}$-HI, $N^{\alpha A1}$-heptanoyl-$Gly^{A21}$-HI, $N^{\epsilon B29}$-octanoyl-$N^{\alpha B1}$-octanoyl-$Gly^{A21}$-HI, $N^{\epsilon B29}$-propionyl-$N^{\alpha A1}$-propionyl-$Gly^{A21}$-HI, $N^{\alpha A1}$-acetyl-$N^{\alpha B1}$-acetyl-$Gly^{A21}$-HI, $N^{\epsilon B29}$-formyl-$N^{\alpha A1}$-formyl-$N^{\alpha B1}$-formyl-$Gly^{A21}$-HI, $N^{\epsilon B29}$-butyryl-des(B30)-HI, $N^{\alpha B31}$-butyryl-des(B30)-HI, $N^{\alpha A1}$-butyryl-des(B30)-HI, $N^{\epsilon B29}$-butyryl-$N^{\alpha B31}$-butyryl-des(B30)-HI, $N^{\epsilon B29}$-butyryl-$N^{\alpha A1}$-butyryl-des(B30)-HI, $N^{\alpha A1}$-butyryl-$N^{\alpha B31}$-butyryl-des(B30)-HI, $N^{\epsilon B29}$-butyryl-$N^{\alpha A1}$-butyryl-$N^{\alpha B31}$-butyryl-des(B30)-HI, $Lys^{B28}Pro^{B29}$-HI (insulin lispro), $Asp^{B28}$-HI (insulin aspart), $Lys^{B3}Glu^{B29}$-HI (insulin glulisine), $Arg^{B31}Arg^{B32}$-HI (insulin glargine), $N^{\epsilon B29}$-myristoyl-des(B30)-HI (insulin detemir), $Ala^{B26}$-HI, $Asp^{B1}$-HI, $Arg^{A0}$-HI, $Asp^{B1}Glu^{B13}$-HI, $Gly^{A21}$-HI, $Gly^{A21}Arg^{B31}Arg^{B32}$-HI, $Arg^{A0}Arg^{B31}Arg^{B32}$-HI, $Arg^{A0}Gly^{A21}Arg^{B31}Arg^{B32}$-HI, des(B30)-HI, des(B27)-HI, des(B28-B30)-HI, des(B1)-HI, des(B1-B3)-HI$N^{\epsilon B29}$-tridecanoyl-des(B30)-HI, $N^{\epsilon B29}$-tetradecanoyl-des(B30)-HI, $N^{\epsilon B29}$-decanoyl-des(B30)-HI, $N^{\epsilon B29}$-dodecanoyl-des(B30)-HI, $N^{\epsilon B29}$-tridecanoyl-$Gly^{A21}$-des(B30)-HI, $N^{\epsilon B29}$-tetradecanoyl-$Gly^{A21}$-des(B30)-HI, $N^{\epsilon B29}$-decanoyl-$Gly^{A21}$-des(B30)-HI, $N^{\epsilon B29}$-dodecanoyl-$Gly^{A21}$-des(B30)-HI, $N^{\epsilon B29}$-tridecanoyl-$Gly^{A21}Gln^{B3}$-des(B30)-HI, $N^{\epsilon B29}$-tetradecanoyl-$Gly^{A21}Gln^{B3}$-des(B30)-HI, $N^{\epsilon B29}$-decanoyl-$Gly^{A21}$-$Gln^{B3}$-des(B30)-HI, $N^{\epsilon B29}$-dodecanoyl-$Gly^{A21}$-$Gln^{B3}$-des(B30)-HI, $N^{\epsilon B29}$-tridecanoyl-$Ala^{A21}$-des(B30)-HI, $N^{\epsilon B29}$-tetradecanoyl-$Ala^{A21}$-des(B30)-HI, $N^{\epsilon B29}$-decanoyl-$Ala^{A21}$-des(B30)-HI, $N^{\epsilon B29}$-dodecanoyl-$Ala^{A21}$-des(B30)-HI, $N^{\epsilon B29}$-tridecanoyl-$Ala^{A21}$-$Gln^{B3}$-des(B30)-HI, $N^{EB29}$-tetradecanoyl-$Ala^{A21}Gln^{B3}$-des(B30)-HI, $N^{\epsilon B29}$-decanoyl-$Ala^{A21}Gln^{B3}$-des(B30)-HI, $N^{\epsilon B29}$-dodecanoyl-$Ala^{A21}Gln^{B3}$-des(B30)-HI, $N^{\epsilon B29}$-tridecanoyl-$Gln^{B3}$-des(B30)-HI, $N^{\epsilon B29}$-tetradecanoyl-$Gln^{B3}$-des(B30)-HI, $N^{\epsilon B29}$-decanoyl-$Gln^{B3}$-des(B30)-HI, $N^{\epsilon B29}$-dodecanoyl-$Gln^{B3}$-des(B30)-HI, $N^{\epsilon B29}$-Z1-$Gly^{A21}$-HI, $N^{\epsilon B29}$-Z2-$Gly^{A21}$-HI, $N^{\epsilon B29}$-Z4-$Gly^{A21}$-HI, $N^{\epsilon B29}$-Z3-$Gly^{A21}$-HI, $N^{\epsilon B29}$-Z1-$Ala^{A21}$-HI, $N^{\epsilon B29}$-Z2-$Ala^{A21}$-HI, $N^{\epsilon B29}$-Z4-$Ala^{A21}$-HI, $N^{\epsilon B29}$-Z3-$Ala^{A21}$-HI, $N^{\epsilon B29}$-Z1-$Gly^{A21}Gln^{B3}$-HI, $N^{\epsilon B29}$-Z2-$Gly^{A21}Gln^{B3}$-HI, $N^{\epsilon B29}$-Z4-$Gly^{A21}Gln^{B3}$-HI, $N^{\epsilon B29}$-Z3-$Gly^{A21}Gln^{B3}$-HI, $N^{\epsilon B29}$-Z1-$Ala^{A21}Gln^{B3}$-HI, $N^{\epsilon B29}$-Z2-$Ala^{A21}Gln^{B3}$-HI, $N^{\epsilon B29}$-Z4-$Ala^{A21}Gln^{B3}$-HI, $N^{\epsilon B29}$-Z3-$Ala^{A21}Gln^{B3}$-HI, $N^{\epsilon B29}$-Z1-$Gln^{B3}$-HI, $N^{\epsilon B29}$-Z2-$Gln^{B3}$-HI, $N^{\epsilon B29}$-Z4-$Gln^{B3}$-HI, $N^{\epsilon B29}$-Z3-$Gln^{B3}$-HI, $N^{\epsilon B29}$-Z1-$Glu^{B30}$-HI, $N^{\epsilon B29}$-Z2-$Glu^{B30}$-HI, $N^{\epsilon B29}$-Z4-$Glu^{B30}$-HI, $N^{EB29}$-Z3-$Glu^{B30}$-HI, $N^{\epsilon B29}$-Z1-$Gly^{A21}Glu^{B30}$-HI, $N^{\epsilon B29}$-Z2-$Gly^{A21}Glu^{B30}$-HI, $N^{\epsilon B29}$-Z4-$Gly^{A21}Glu^{B30}$-HI, $N^{\epsilon B29}$-Z3-$Gly^{A21}Glu^{B30}$-HI, $N^{\epsilon B29}$-Z1-$Gly^{A21}Gln^{B3}Glu^{B30}$-HI, $N^{\epsilon B29}$-Z2-$Gly^{A21}Gln^{B3}Glu^{B30}$-HI, $N^{\epsilon B29}$-Z4-$Gly^{A21}Gln^{B3}Glu^{B30}$-HI, $N^{\epsilon B29}$-Z3-$Gly^{A21}Gln^{B3}Glu^{B30}$-HI, $N^{\epsilon B29}$-Z1-$Ala^{A21}Glu^{B30}$-HI, $N^{\epsilon B29}$-Z2-$Ala^{A21}Glu^{B30}$-HI, $N^{\epsilon B29}$-Z4-$Ala^{A21}Glu^{B30}$-HI, $N^{\epsilon B29}$-Z3-$Ala^{A21}Glu^{B30}$-HI, $N^{\epsilon B29}$-Z1-$Ala^{A21}Gln^{B3}Glu^{B30}$-HI, $N^{\epsilon B29}$-Z2-$Ala^{A21}Gln^{B3}Glu^{B30}$-HI, $N^{\epsilon B29}$-Z4-$Ala^{A21}Gln^{B3}Glu^{B30}$-HI, $N^{\epsilon B29}$-Z3-$Ala^{A21}Gln^{B3}Glu^{B30}$-HI, $N^{\epsilon B29}$-Z1-$Gln^{B3}Glu^{B30}$-HI, $N^{\epsilon B29}$-Z2-$Gln^{B3}Glu^{B30}$-HI, $N^{\epsilon B29}$-Z4-$Gln^{B3}Glu^{B30}$-HI, $N^{\epsilon B29}$-Z3-

$Gln^{B3}Glu^{B30}$-HI and where Z1 is tridecanoyl, Z2 is tetradecanoyl, Z3 is dodecanoyl and Z4 is decanoyl and HI is human insulin.

In certain embodiments, an insulin molecule has the following mutations and/or chemical modifications: $N^{\epsilon B28}$-XXXXX-Lys$^{B28}$Pro$^{B29}$-HI, $N^{\alpha B1}$-XXXXX-Lys$^{B28}$Pro$^{B29}$-HI, $N^{\alpha A1}$-XXXXX-Lys$^{B28}$Pro$^{B29}$-HI, $N^{\epsilon B28}$-XXXXX-$N^{\alpha B1}$-XXXXX-Lys$^{B28}$Pro$^{B29}$-HI, $N^{\epsilon B28}$-XXXXX-$N^{\alpha A1}$-XXXXX-Lys$^{B28}$Pro$^{B29}$-HI, $N^{\alpha A1}$-XXXXX-$N^{\alpha B1}$-XXXXX-Lys$^{B28}$Pro$^{B29}$-HI, $N^{\epsilon B28}$-XXXXX-$N^{\alpha A1}$-XXXXX-$N^{\alpha B1}$-XXXXX-Lys$^{B28}$Pro$^{B29}$-HI, $N^{\epsilon B29}$-XXXXX-HI, $N^{\alpha B1}$-XXXXX-HI, $N^{\alpha A1}$-XXXXX-HI, $N^{\epsilon B29}$-XXXXX-$N^{\alpha B1}$-XXXXX-HI, $N^{\epsilon B29}$-XXXXX-$N^{\alpha A1}$-XXXXX-HI, $N^{\alpha A1}$-XXXXX-$N^{\alpha B1}$-XXXXX-HI, $N^{\epsilon B29}$-XXXXX-$N^{\alpha A1}$-XXXXX-$N^{\alpha B1}$-XXXXX-HI, $N^{\epsilon B29}$-YYYYY-HI, $N^{\alpha B1}$-YYYYY-HI, $N^{\alpha A1}$-YYYYY-HI, $N^{\epsilon B29}$-YYYYY-$N^{\alpha B1}$-YYYYY-HI, $N^{\epsilon B29}$-YYYYY-$N^{\alpha A1}$-YYYYY-HI, $N^{\alpha A1}$-YYYYY-$N^{\alpha B1}$-YYYYY-HI, $N^{\epsilon B29}$-YYYYY-$N^{\alpha A1}$-YYYYY-$N^{\alpha B1}$-YYYYY-HI, $N^{\epsilon B28}$-YYYYY-Lys$^{B28}$Pro$^{B29}$-HI, $N^{\epsilon B21}$-YYYYY-Lys$^{B28}$Pro$^{B29}$-HI, $N^{\alpha A1}$-YYYYY-Lys$^{B28}$Pro$^{B29}$-HI, $N^{\epsilon B28}$-YYYYY-$N^{\alpha B1}$-YYYYY-Lys$^{B28}$Pro$^{B29}$-HI, $N^{\epsilon B28}$-YYYYY-$N^{\alpha A1}$-YYYYY-Lys$^{B28}$Pro$^{B29}$-HI, $N^{\alpha A1}$-YYYYY-$N^{\alpha B1}$-YYYYY-Lys$^{B28}$Pro$^{B29}$-HI, $N^{\epsilon B28}$-YYYYY-$N^{\alpha A1}$-YYYYY-$N^{\alpha B1}$-YYYYY-Lys$^{B28}$Pro$^{B29}$-HI, and where YYYYY is one of acetyl or formyl and where XXXXX is one of: propionyl, butyryl, pentanoyl, hexanoyl, heptanoyl, octanoyl, nonanoyl or decanoyl and HI is human insulin.

As discussed herein, the insulin molecule may be conjugated through a reactive moiety that is naturally present within the insulin structure or added prior to conjugation, including, for example, carboxyl or reactive ester, amine, hydroxyl, aldehyde, sulfhydryl, maleimidyl, alkynyl, azido, etc. moieties. Insulin naturally includes reactive alpha-terminal amine and epsilon-amine lysine groups to which NHS-ester, isocyanates or isothiocyanates can be covalently conjugated. In certain embodiments, a modified insulin may be employed in which a suitable amino acid (e.g., a lysine or a non-natural amino acid) has been added or substituted into the amino acid sequence in order to provide an alternative point of conjugation. In addition, as discussed in more detail below, it will be appreciated that the conjugation process may be controlled by selectively blocking certain reactive moieties prior to conjugation. It is to be understood that insulin may include any combination of these modifications and the present disclosure also encompasses modified forms of non-human insulins (e.g., porcine insulin, bovine insulin, rabbit insulin, sheep insulin, etc.) that comprise any one of the aforementioned modifications. It is understood that certain embodiments may include these and certain other previously described modified insulins such as those described in U.S. Pat. Nos. 5,474,978; 5,461,031; 4,421,685; 7,387,996; 6,869,930; 6,174,856; 6,011,007; 5,866,538; 5,750,4976; 906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; US20150353619, including non-natural amino acids described or referenced herein and including such modifications to the non-human insulins described herein. It is also to be understood that in certain embodiments the insulin may be covalently conjugated to polyethylene glycol polymers of no more than Mn218,000, or covalently conjugated to albumin.

In certain embodiments glucagon, the sequence of human glucagon protein has the amino acid sequence: HSQGTFTSDYSKYLDSRRAQDFVQWLMNT (SEQ ID NO: 13) or the entire or part or any contiguous amino acid sequence of at least 7 residues within:

```
                                          (SEQ ID NO: 14)
MKSIYFVAGLFVMLVQGSWQRSLQDTEEKSRSFSASQADPLSDPDQMNEDK

RHSQGTFTSDYSKYLDSRRAQDFVQWLMNTKRNRNNIAKRHDEFERHAEGT

FTSDVSSYLEGQAAKEFIAWLVKGRGRRDFPEEVAIVEELGRRHADGSFSD

EMNTILDNLAARDFINWLIQTKITDRK.
```

GLP-1 sequences: HAEGTFTSDV SSYLEGQAAK EFIAWLVKGR G (SEQ ID NO: 15), or sequence HDEFERHAEGTFTSDVSSYLEGQAAKEFIAWLVKGR-NH$_2$ (SEQ ID NO: 16) or GLP-2 sequence: HADGSFSDEMNTILDNLAARDFINWLIQTKITD (SEQ ID NO: 17) including variation of these with deletions, insertions and replacements of one or more amino acids. In certain embodiment modifications made to insulin discussed herein can be made to glucagon.

It is contemplated that the invention will contain conjugates in which different units are linked together, such as, for example, a polymer linked to an insulin; a polymer linked to a protein; a polymer linked to a decoy ligand; a polymer linked to a glucose-binding agent; any subsection of a polymer linked to the remaining section of a polymer.

Linker conjugation chemistries and molecular characteristics can be tested using SDS-polyacrylamide gel shift assays to verify conjugation and correct stoichiometry. Different linker chemistries and end functionalizations can be tested. For example, depending on the artificial amino acids used, a terminal alkyne or azide can be present on a polypeptide in certain embodiments described herein. To selectively conjugate the terminal azides and alkynes one can perform the copper-catalyzed 3+2 cycloaddition reaction (click reaction) using appropriate copper-coordinating ligands, as for example described by: Rostovtsev, V. V., Green, L. G., Fokin, V. V. & Sharpless, K. B. A stepwise huisgen cycloaddition process: copper(I)-catalyzed regioselective "ligation" of azides and terminal alkynes. Angew. Chem. Int. Ed. 41, 2596-2599 (2002). In addition, copper free conjugation of terminal azides to alkyne or alkynyl probes can be used as described by: Liang, Y., Mackey, J. L., Lopez, S. A., Liu, F. & Houk, K. N. Control and design of mutual orthogonality in bioorthogonal cycloadditions. J. Am. Chem. Soc. 134, 17904-17907 (2012) and Beatty, K. E. et al. Live-cell imaging of cellular proteins by a strain-promoted azide-alkyne cycloaddition. Chembiochem 11, 2092-2095 (2010). Cyclooctynes are particularly useful because their fast reaction kinetics, copper free reaction conditions and enable near quantitative conjugation.

As described above, the decoy ligand is a molecule to which the glucose-binding agent can bind. In some embodiments, the decoy ligand may bind to the active site of the glucose-binding agent which is the same site that binds to glucose. In another embodiment the decoy ligand binds elsewhere on the glucose-binding agent and not to the active site to which glucose binds. In one embodiment the decoy ligand can be a peptide with less than 50 amino acids and such peptide may include any of the non-natural amino acids described or referenced to herein, including L or D amino acids. In certain embodiments the decoy ligand can be a cyclic peptide.

A peptide decoy ligand may be selected by affinity chromatography or by positive selection with a target glucose-binding protein, or negative selection against other sequences or at the highest glucose concentrations. After selection, a library of decoy ligands is developed through, for example, combinatorial peptide synthesis, phage display, yeast surface display or mRNA display. The library is then selected to bind the glucose-binding agent at a given glucose concentration. This process can be repeated each time either a new library is generated or a modified library of peptide sequences is generated based on the sequences of peptides that bind to the glucose-binding agent. One skilled in the art will recognize that it is possible to make modifications to this library development and selection process in order to obtain a decoy ligand that binds to the glucose-binding agent with a specific affinity at a given glucose concentration. In one embodiment the decoy ligand is a polypeptide. In one embodiment the decoy ligand is albumin.

In certain embodiments the decoy ligand is a peptide that is further modified through covalent conjugation by linking to a chemical structure described by formula F1 or formula F2. In certain embodiments the decoy ligand is a chemical structure described by formula F1 or formula F2:

F1

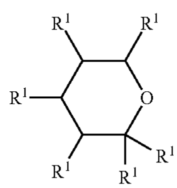

F2 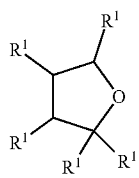 wherein:

each $R^1$ can independently have (R) or (S) stereochemistry and is independently selected from —H, —$OR^3$, —$N(R^3)_2$, —$SR^3$, —OH, —$OCH_3$, —$OR^5$, —$R^6$—$R^7$, —$NHC(O)CH_3$, —$CH_2R^3$, —$NHC(O)CH_3$, —$CH_2OH$, —$CH_2OR^5$, —$NH_2$ or —$CH_2R^4$ each $R^2$ is independently selected from —H or an optionally substituted group selected from $C_{1-6}$ aliphatic, phenyl, a 5-6 membered monocyclic heteroaryl ring having 1-4 heteroatoms selected from nitrogen, oxygen, or sulfur, or a 4-7 membered heterocyclic ring having 1-2 heteroatoms selected from nitrogen, oxygen, or sulfur each $R^3$ is independently selected from —H, acetyl, phosphate, —$R^2$, —$SO_2R^2$, —$S(O)R^2$, —$P(O)(OR^2)_2$, —$C(O)R^2$, —$CO_2R^2$, or —$C(O)N(R^2)_2$ each $R^4$ is independently selected from —H, —OH, —$OR^3$, —$N(R^3)_2$, —$OR^5$ or —$SR^3$;

each $R^5$ is independently selected from either a mono- di- or tri-saccharide, a pentose or a hexose each $R^6$ is independently selected from a linker, —$NCOCH_2$—, —$OCH_2CH_2$—, —O—$C_{1-9}$ alkylene, a substituted $C_{1-9}$ alkylene in which one or more methylene is optionally replaced by —O—, —$CH_2$—, —$OCH_2$—, —$N(R^2)C(O)$—, —$N(R^2)C(O)N(R^2)$—, —$SO_2$—, —$SO_2N(R^2)$—, —$N(R^2)SO_2$—, —S—, —$N(R^2)$—, —C(O)—, —OC(O)—, —C(O)O—, —$C(O)N(R^2)$—, or —$N(R^2)SO_2N(R^2)$— each $R^7$ is independently selected from —$N(R^2)_2$, —F, —Cl, —Br, —I, —SH, —$OR^2$, —$SR^2$, —$NH_2$, —$N_3$, —C≡$CR^2$, —$CH_2$C≡CH, —C≡CH, —$CO_2R^2$, —C(O)$R^2$, or —$OSO_2R^2$. —$N(R^2)_2$, —$OR^2$, —$SR^2$ or —$CH_2NH_2$ In certain embodiments the glycosidic bond resulting from —$OR^5$ connected to an anomeric carbon can be in the α: DOWN or β: UP configuration.

In certain embodiments the decoy ligand contains an azido diol. In certain embodiments, the decoy ligand is a monosaccharide, disaccharide, trisaccharide or polysaccharide. In certain embodiments, the decoy ligand can have up to 10 saccharides. In some embodiments, the decoy ligand comprises a saccharide and one or more amine groups. In some embodiments, the decoy ligand is aminoethylglucose, aminoethylbimannose aminoethyltrimannose. In certain embodiments the decoy ligand is D-glucose, D-galactose, D-Allose, D-Mannose, D-Gulose, D-Idose, D-Talose, N-Azidomannosamine (ManNAz) orN-Azidogalactoseamine (GalNAz) or N-azidoglucoseamine (GlcNAz), 2'-fluororibose, 2'-deoxyribose, glucose, sucrose, maltose, mannose, derivatives of these (e.g., glucosamine, mannosamine, methylglucose, methylmannose, ethylglucose, ethylmannose, etc.) and/or higher order combinations of these (such as linear and/or branched bimannose, linear and/or branched trimannose). In certain embodiments the decoy ligand contains a DOPA molecule such as L-DOPA or L-3,4-dihydroxyphenylalanine. In certain embodiments such DOPA molecules may be used in a decoy ligand because the DOPA molecule may bind to boronates more effectively than glucose and thereby provide a high-affinity decoy ligand. In certain embodiments the decoy ligand is a sugar alcohol, a sugar alcohol is defined as a $C_4$-$C_8$ hydrocarbon having at least one —OH group. Examples of sugar alcohols include mannitol, sorbitol, inositol, galactitol, dulcitol, xylitol, and arabitol.

In certain embodiments the decoy ligand is a modified form of glucose such as an azidoglucose. For example, M-Azido-M-deoxy-D-glucose where M is one of 1, 2, 3, 4, 5, 6. In certain embodiments, the decoy ligand is an azide containing sugar and the azide containing sugar can, for example, be linked through click chemistry with a terminal alkyne (such terminal alkyne may, for example, be present as a side chain of an amino acid in the one or more polymer, wherein the amino acid is a non-natural amino acid such as L-homopropargylglycine or other amino acids described herein with alkyne side chains). The azide group on the sugar can be linked to an alkyne group by, for example, copper catalyzed click reaction resulting in a triazole linkage, or linked to a cyclooctyne which in certain embodiments is itself linked to a side chain of an amino acid.

In certain embodiments, an artificial amino acid may be included in the polymer, insulin, decoy ligand, or glucose-binding agent. There are 20 different natural (canonical) amino acids that are the building-blocks of all natural proteins. Non-canonical amino acids or artificial amino acids have side chains that are distinct from canonical amino acids and are not normally present in proteins. The incorporation of artificial amino acids into recombinant proteins, or synthesized peptides, enables introduction of chemical groups that can be selectivity functionalized and modified. This is particularly useful for development of modified insulins because it enables selective chemical modifications of insulin at specified positions in the protein sequence. Similarly, in certain embodiments in which the decoy ligand or glucose-binding agent have amino acids, the use of artificial amino acids allows for cites of conjugations of modification of physical properties. In certain embodiments, artificial amino acids can be used to modulate pKa, local hydrophobicity of protein domains as well as aggregation and folding properties, or to introduce new chemistries or chemical and or physical properties including thermostability, aggregation behavior, solution stability, reduced aggregation, conformation changes and or movements of A and B chains of insulin with respect to each other. In certain embodiments, one or more of the following proteinogenic artificial amino acids described by formulas F26-F41 may be used:

F26
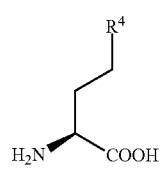

F27
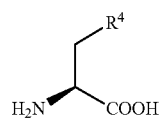

F28
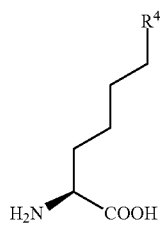

F29
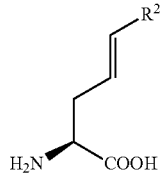

F30
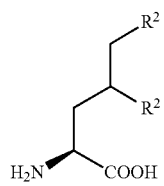

F31
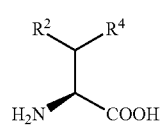

F32
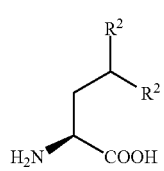

F33
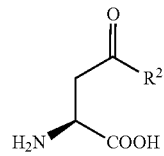

F34
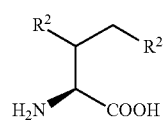

F35
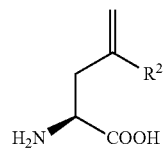

F36
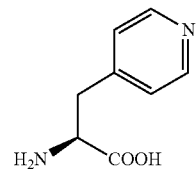

F37
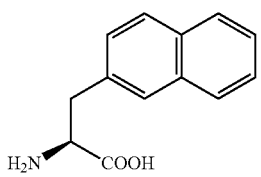

F38
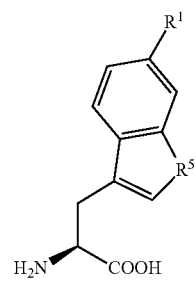

F39
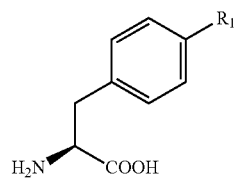

F40
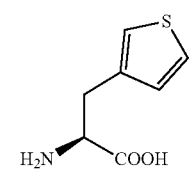

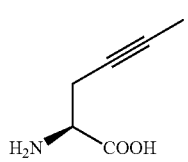

wherein:
each $R^1$ is independently selected from —H, —NH$_2$, —NO$_2$, —Cl, —CF$_3$, —I, —COCH$_3$, —CN, —C≡CH, —N$_3$, or —Br
each $R^2$ is independently selected from —CF$_3$, —H, or —CH$_3$
each $R^3$ is independently selected from —C≡CH, —H, —N$_3$, or vinyl group
each $R^4$ is independently selected from $R^2$ or $R^3$
each $R^5$ is independently selected from —S— or —NH—

Moreover, one skilled in the art recognizes that in certain embodiments, one or more of the previously published proteinogenic artificial amino acids can be used. For example, in certain embodiments one or more of the following artificial amino acids can be used based on method described in and referenced through, and the list of amino acid provided in: Liu, C. C.; Schultz, P. G. (2010). "Adding new chemistries to the genetic code". Annual Review of Biochemistry 79: 413-44. One skilled in the art recognizes that artificial amino acids can be incorporated by peptide synthesis and these include the amino acids referenced herein as well as previously reported non-proteinogenic amino acids. For example, but not limited to, a portfolio of such non-proteinogenic amino acids including β-amino acids is available commercially from Sigma Aldrich.

As an example, proteinogenic artificial amino acids described in F26-F41 can be incorporated through recombinant protein expression using methods and approaches described in U.S. patent and patent applications including: US20080044854, U.S. Pat. Nos. 8,518,666, 8,980,581, US20080044854, US20140045261, US20040053390, U.S. Pat. Nos. 7,229,634, 8,236,344, US20050196427, US20100247433, U.S. Pat. Nos. 7,198,915, 7,723,070, US20020042097, US20040058415, US20080026422, US20080160609, US20100184193, US20120077228, US2014025599, U.S. Pat. Nos. 7,198,915, 7,632,492, 7,723, 070, as well as other proteinogenic artificial amino acids may be introduced recombinantly using methods and approaches described in: U.S. Pat. Nos. 7,736,872, 7,816, 320, 7,829,310, 7,829,659, 7,883,866, 8,097,702, 8,946,148.

In certain embodiments cyclic amino acid such as 3-hydroxyproline, 4-hydroxyproline, aziridine-2-earboxylic acid, azetidine-2-carboxylic acid, piperidine-2-carboxyJic acid, 3-carboxy-morpholine, 3-carboxy-thiamorpholine, 4-oxaproline, pyroglutamic acid, 1,3-oxazolidine-4-carboxylic acid, 1,3-thiazolidine-4-carboxyiic acid, 3-thiaproline, 4-thiaproline, 3-selenoproline, 4-selenoproline, 4-ketoproiine, 3,4-dehydroproline, 4-aminoproline, 4-fluoroproline, 4,4-difluoroproline, 4-ehloroproiine, 4,4-dichloroproline, 4-bromoproiine, 4,4-dibromoproline, 4-methylproline, 4-ethylprofine, 4-cyclohexyl-proiine, 3-plienylproline, 4-phenylproline, 3,4-phenyfproline, 4-azidoproline, 4-carboxy-proline, a-methylproline, a-ethylproline, a-propylproline, a-allylproline, a-benzy[proline, a-(4~fluorobenzyl)~proline, a-(2-chlorobenzyi)-proline, a-(3-chlorobenzyl)-proline, a-(2-bromobenzy)-proline, a-(4-bromobenzyl)-proline, a-(4-methylbenzyl)-proline, a-(diphenylmethyl)-proline, a-(naphthylmethy3)-proime, D-proline, or J-homoproline, (2S,4S)-4-fluoro-L-proline, (2S,4R)-4-fluoro-L-proline, (2S)-3,4-dehydro-L-pro3ine, (2S,4S)-4-hydroxy-L-proline, (2S,4R)-4-hydroxy-L-proline, (2S,4S)-4-azido-L-proline, (2S)-4,4-difluoro-L-proline, (2S)-azetidine-2-carboxylic acid, (2S)-piperidine-2-carboxylic acid, or (4R)-1,3-thiazolidine-4-carboxylic acid can be used in the one or more polymers, insulin or the decoy ligands or glucose-binding agents.

In certain embodiments artificial amino acids that are methionine analogues are introduced to recombinantly expressed proteins. For example, a methionine analogue is introduced to insulins. The codon coding for methionine (ATG) is introduced at position of interest in the DNA sequence that codes for insulin. As mature wild type human insulin does not have a methionine, this approach provides a position for the introduction of artificial amino acids which is coded for using methionine codon. The codon for methionine can replace a given codon in the insulin coding sequence, in which case the amino acid coded for by that codon is replaced by methionine. The DNA sequence can be part of an expression vector for expression of insulin using recombinant DNA technology. For example, the insulin can be expressed in a BL21 *E. coli* expression strain using the pQE80 expression vector. During heterologous protein expression of insulin, a media replacement approach can be used to deplete the media of methionine and introduce the methionine surrogate of interest during insulin expression. One skilled in the art can therefore easily use this procedure to develop a recombinantly expressed insulin, decoy ligand or glucose-binding agent to contain a proteinogenic artificial amino acid. For example, the methionine analogue can be azidohomoalanine, represented by formula F26 where $R^4$ is $R^3$ and $R^3$ is —N$_3$. The azide introduced in this manner can be used for conjugation by click chemistry and as described herein.

Additionally, incorporation of artificial amino acids can be checked by reaction of the side chain of the artificial amino acid with dyes, or for example using methods known in the art such as tryptic digestion and MALDI-TOF mass spectrometry. One skilled in the art also recognizes that to recombinantly express insulins, glucose-binding agents or decoy ligands containing proteinogenic artificial amino acids, one can also use any of widely used protein expression hosts such as *S. cerevisiae* and *Pichia pastoris* or *E. coli* expression strains.

The one or more polymers used in the present invention have, for example, at least 3 monomers and no more than 100,000 monomers, where the monomers can independently be the same or different. In certain embodiments the one or more polymer is an alternating polymer, periodic polymer, statistical copolymer or block copolymer. In one embodiment the monomers of the one or more polymer are amino acids, in which case the polymer is a polypeptide. In certain embodiments, the polymer contains segments of polypeptides or peptides and segments of synthetic polymers. In certain embodiments, at least one of the one or more polymers is a polymer of ethylene oxide or PEG. In some embodiments, the polymer is composed of a segments of PEG and peptides or polypeptides connected together as a copolymer or alternating polymer. The one or more polymer can in some embodiments contain one or more copies of the non-natural amino acid p-boronophenyl alanine, such as, for example, a peptide sequence consisting of natural amino acids and one or more of p-boronophenylalanine. In certain embodiments the one or more polymer may contain one or more artificial amino acids.

In certain embodiments, the one or more polymer is covalently conjugate to insulin is additional covalently conjugate to human glucokinase or a protein with at least 70% homology to the human glucokinase protein. The human glucokinase protein has the amino acid sequence: MLDDRARMEAAKKEKVEQILAEFQLQEEDLKKVMRRMQKEMDRGLRLETHEEASVK MLPTYVRSTPEGSEVGDFLSLDLGGTNFRVMLVKVGEGEEGQWSVKTKHQMYSIPED AMTGTAEMLFDYISECISDFLDKHQMKHKKLPLGFTFSFPVRHEDIDKGILLNWTKGF KASGAEGNNVVGLLRDAIKRRGDFEMDVVAMVNDTVATMISCYYEDHQCEVGMIVG TGCNACYMEEMQNVELVEGDEGRMCVNTEWGAFGDSGELDEFLLEYDRLVDESSAN PGQQLYEKLIGGKYMGELVRLVLLRLVDENLLFHGEASEQLRTRGAFETRFVSQVESD TGDRKQIYNILSTLGLRPSTTDCDIVRRACESVSTRAAHMCSAGLAGVINRMRESRSED VMRITVGVDGSVYKLHPSFKERFHASVRRLTPSCEITFIESEEGSGRGAALVSAVACKK ACMLGQ (SEQ ID NO:4). In certain embodiments the decoy ligand can bind to the glucose-binding pocket of glucokinase and in the bound configuration cause chain movements described herein to disrupt binding of insulin to the insulin receptor. In certain embodiments, chain movements that occur in glucokinase as it binds to soluble glucose are transferred to chain movement in insulin or one or more polymer conjugated to insulin and thereby control insulin activity. It is to be understood that glucokinase is sometimes referred to as hexokinase IV and herein the term glucokinase is meant to include mutants of glucokinase, different organ specific isoforms or sequences of glucokinase that include artificial amino acids. Similarly, the mechanisms and descriptions given herein for glucokinase, certain embodiments use the same mechanisms and constructions but instead of glucokinase use one of the hexokinase I, II or III in humans. For example, in one embodiment the one or more polymer that is covalently conjugated to insulin is covalently linked to, or comprises of, human hexokinase I. The sequence for human hexokinase 1 is MIAAQLLAYYFTELKDDQVKKIDKYLYAMRLSDETLIDIMTRFRKEMKNGLSRDFNPT ATVKMLPTFVRSIPDGSEKGDFIALDLGGSSFRILRVQVNHEKNQNVHMESEVYDTPE NIVHGSGSQLFDHVAECLGDFMEKRKIKDKKLPVGFTFSFPCQQSKIDEAILITWTKRF KASGVEGADVVKLLNKAIKKRGDYDANIVAVVNDTVGTMMTCGYDDQHCEVGLIIG TGTNACYMEELRHIDLVEGDEGRMCINTEWGAFGDDGSLEDIRTEFDREIDRGSLNPG KQLFEKMVSGMYLGELVRLILVKMAKEGLLFEGRITPELLTRGKFNTSDVSAIEKNKE GLHNAKEILTRLGVEPSDDDCVSVQHVCTIVSFRSANLVAATLGAILNRLRDNKGTPRL RTTVGVDGSLYKTHPQYSRRFHKTLRRLVPDSDVRFLLSESGSGKGAAMVTAVAYRL AEQHRQIEETLAHFHLTKDMLLEVKKRMRAEMELGLRKQTHNNA VVKMLPSFVRRT PDGTENGDFLALDLGGTNFRVLLVKIRSGKKRTVEMHNKIYAIPIEIMQGTGEELFDHI VSCISDFLDYMGIKPRMPLGFTFSFPCQQTSLDAGILITWTKGFKATDCVGHDVVTLL RDAIKRREEFDLDVVAVVNDTVGTMMTCAYEEPTCEVGLIVGTGSNACYMEEMKNV EMVEGDQGQMCINMEWGAFGDNGCLDDIRTHYDRLVDEYSLNAGKQRYEKMISGM YLGEIVRNILIDFTKKGFLFRGQISETLKTRGIFETKFLSQIESDRLALLQVRAILQQLGLN STCDDSILVKTVCGVVSRRAAQLCGAGMAAVVDKIRENRGLDRLNVTVGVDGTLYK LHPHFSRIMHQTVKELSPKCNVSFLLSEDGSGKGAALITAVGVRLRTEASS (SEQ ID NO:5) and it is to be understood that certain amino acid modifications such as presence of N-acetylmethionine at residues 1 or phosphserine at residues 337 may be present in these proteins. The term hexokinase I includes any protein with at least 70% homology to the amino acid sequence for hexokinase I provided herein. In certain embodiments the glucose-binding agent is a glucose-binding protein including one of human hexokinase I, II, III, IV. The amino acid sequence for human hexokinase II is MIASHLLAYFFTELNHDQVQKVDQYLYHMRLSDETLLEISKRFRKEMEKGLGATTHPT AAVKMLPTFVRSTPDGTEHGEFLALDLGGTNFRVLWVKVTDNGLQKVEMENQIYAIP EDIMRGSGTQLFDHIAECLANFMDKLQIKDKKLPLGFTFSFPCHQTKLDESFLV SWTKG FKSSGVEGRDVVALIRKAIQRRGDFDIDIVAVVNDTVGTMMTCGYDDHNCEIGLIVGT GSNACYMEEMRHIDMVEGDEGRMCINMEWGAFGDDGSLNDIRTEFDQEIDMGSLNP GKQLFEKMISGMYMGELVRLILVKMAKEELLFGGKLSPELLNTGRFETKDISDIEGEKD GIRKAREVLMRLGLDPTQEDCVATHRICQIVSTRSASLCAATLAAVLQRIKENKGEERL RSTIGVDGSVYKKHPHFAKRLHKTVRRLVPGCDVRFLRSEDGSGKGAAMVTAVAYRL ADQHRARQKTLEHLQLSHDQLLEVKRRMKVEMERGLSKETHASAPVKMLPTYVCAT PDGTEKGDFLALDLGGTNFRVLLVRVRNGKWGGVEMHNKIYAIPQEVM HGTGDELF DHIVQCIADFLEYMGMKGVSLPLGFTFSFPCQQNSLDESILLKWTKGFKASGCEGEDV VTLLKEAIHRREEFDLDVVAVVTSIDTVGTMMTCGFEDPHCEVGLI VGTGSNACYMEEM RNVELVEGEEGRMCVNMEWGAFGDNGCLDDFRTEFDVAVDELSLNPGKQRFEKMIS GMYLGEIVRNILIDFTKRGLLFRGRISERLKTRGIFETKFLSQIESDCLALLQVRAILQHL GLESTCDDSIIVKEVCTVVARRAAQLCGAGMAAVVDRIRENRGLDALKVTVGVDGTL YKLHPHFAKVMHETVKDLAPKCDVSFLQSEDGSGKGAALITAVACRIREAGQR (SEQ ID NO:6) The amino acid sequence for human hexokinase III is: MDSIGSSGLRQGEETLSCSEEGLPGPSDSSELVQECLQQFKVTRAQLQQIQASLLGSME Q ALRGQASPAPAVRMLPTYVGSTPHGTEQGDFVVLELGATGASLRVLWVTL TGIEGHRVEPRSQEFVIPQEVMLGAGQQLFDFAAHCLSEFLDAQPVNKQGLQLGFSFSF PCHQTGLDRSTLISWTKGFRCSGVEGQDVVQLLRDAIRRQGAYNIDVVAVVNDTVGT MMGCEPGVRPCEVGLVVDTGTNACYMEEARHVAVLDEDRGRVCVSVEWGSFSDDG ALGPVLTTFDHTLDHESLNPGAQRFEKMIGGLYLGELVRLVLAHLARCGVLFGGCTSP ALLSQGSILLEHVAEMEDPSTGAARVHAILQDLGLSPGASDVELVQHVCAAVCTRAAQ LCAAALAAVLSCLQHSREQQTLQVAVATGGRVCERHPRFCSVLQGTVMLLAPECDVS LIPSVDGGGRGVAMVTAVAARLAAHRRLLEETLAPFRLNHDQLAAVQAQMRKAMAK GLRGEASSLRMLPTFVRATPDGSERGDFLALDLGGTNFRVLL VRVTTGVQITSEIYSIPE TVAQGSGQQLFDHIVD-CIVDFQQKQGLSGQSLPLGFTFSFPCRQLGLDQGILL NWTKGF KASDCEGQDVVSLL-REAITRRQAVELNVVAIVNDTVGTMMSCGYEDPR-CEIGLIVGTG TNACYMEELRNVAGVPGDSGRMCIN-MEWGAFGDDGSLAMLSTRFDASVDQASINPG KQRFEKMISGMYLGEIVRHILLHLTSLGVL-FRGQQIQRLQTRDIFKTKFLSEIESDSLALR QVRAILEDLGLPLTSD-DALMVLEVCQAVSQRAAQLCGAGVAAVVEKIRENR-GLEELA VSVGVDGTLYKLHPRFSSLVAATVREL-APRCVVTFLQSEDGSGKGAALVTAVACRLA QLTRV (SEQ ID NO:7). In certain embodiments, peptide fragments or specific binding pockets of human hexokinase I, II, III or IV are used as the glucose-binding agent. In certain embodiment the one or more polymers covalently conjugates to insulin contain one or more copies of the amino acid sequence VPGXG (SEQ ID NO:8) where X is any amino acid including artificial amino acids.

The glucose-binding agent includes molecules that can bind to glucose. In certain embodiments the glucose-binding agent can also bind to molecules other than glucose. In one embodiment the glucose-binding agent can include the active site of a glucose-binding protein or a glucose-binding proteins in its entirety. It is to be understood that in certain embodiments, a specific orientation of amino acids is achieved within an active side of a protein through either judicious choice of amino acids, directed evolution of the protein or protein fragment or by site directed mutagenesis of the key residues to yield a specific set of amino acids that allow for glucose-binding. In certain cases the glucose-binding agent can be synthesized by peptide synthesis as for example described by Albericio, F. (2000). Solid-Phase Synthesis: A Practical Guide (1 ed.). Boca Raton: CRC Press, p. 848.

In certain embodiments the glucose-binding agent can bind to insulin. In certain embodiments the glucose-binding pocket of the glucose-binding agent is within the same segment, or within 10 Angstroms of its binding pocket for insulin. In certain embodiments the glucose-binding agent binding pocket for glucose and the glucose-binding agent binding pocket for insulin are different binding pockets in the glucose-binding agent. In certain embodiments the glucose-binding agent can bind to albumin. In certain embodiments the glucose-binding region of the glucose-binding agent is within the same segment, or within 10 Angstroms of its binding region for albumin. In certain embodiments the glucose-binding agent binding pocket for glucose and the glucose-binding agent binding region for albumin are different binding regions in the glucose-binding agent. In certain embodiments the glucose-binding agent includes one or more copies of the non-natural amino acid. For example, in certain embodiments, the non-natural amino acid p-boronophenylalanine can be incorporated into a peptide sequence of the glucose-binding agent.

In certain embodiments the glucose-binding agent is a peptide that is further modified through covalent conjugation by a linker to a chemical structure described by formula F3 or formula F4. In certain embodiments the glucose-binding agent is a chemical structure described by formula F3 or formula F4:

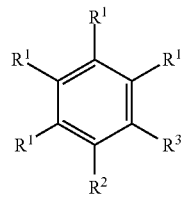

F3

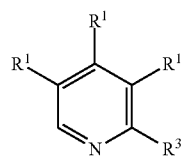

F4 wherein:
each $R^1$ is independently selected from —H, —F, —Cl, —CH$_3$, —B(OH)$_2$, —C≡N, —NO$_2$, or —R$^4$ each $R^2$ is independently selected from —H, —C≡N, —(SO$_2$)NH(R$^4$), or —R$^4$ each $R^3$ is independently selected from —C≡N, —CONH(R$^4$), —NH(R$^4$), —(SO$_2$)NH(R$^4$), or —R$^4$ each $R^4$ is independently selected from —H, —N$_3$, —C≡CH, —CH$_2$N(R$^5$) or a linker each $R^5$ is independently selected from —H or a linker In certain embodiments the glucose-binding agent includes chemical structures described by formulas F5-F25.

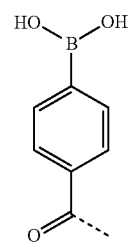

F5

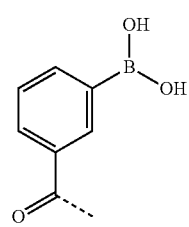

F6

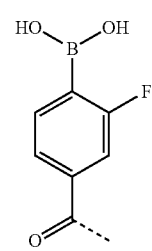

F7

-continued
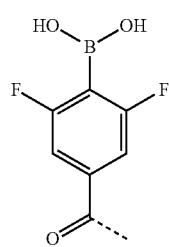 F8
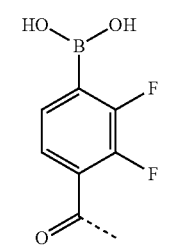 F9
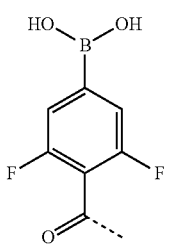 F10
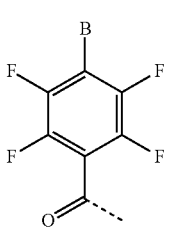 F11
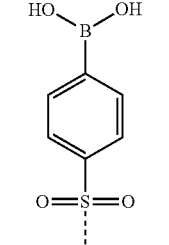 F12
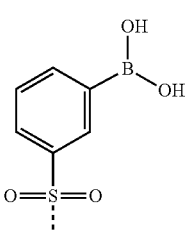 F13
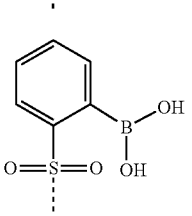 F14
-continued
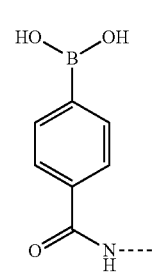 F15
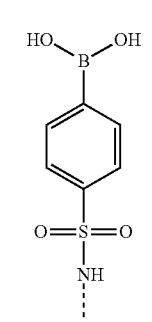 F16
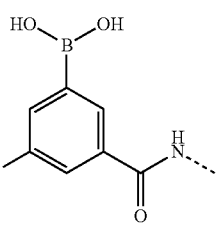 F17
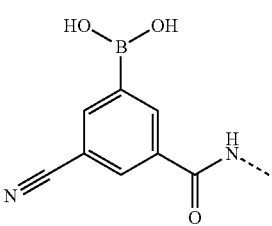 F18
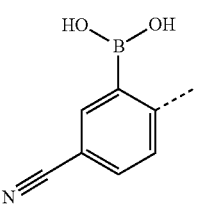 F19
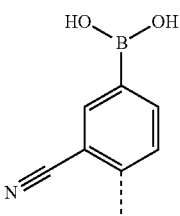 F20

-continued

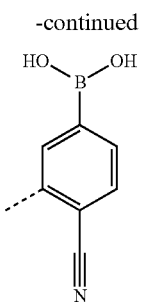
F21

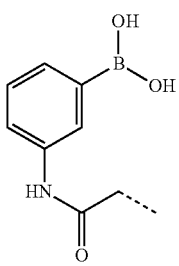
F22

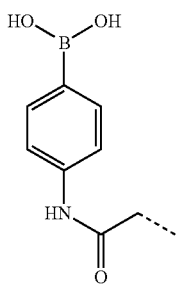
F23

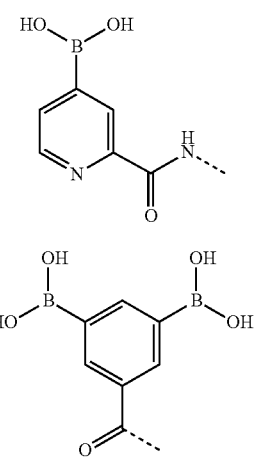
F24

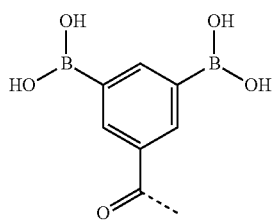
F25

One skilled in the art will recognize that it is possible to make any previously reported, or widely accepted boronate modifications to the chemical structures discussed in F3-F25. In certain embodiments such modifications may include the use of an N-methyliminodiacetic acid (MIDA) group to make a MIDA conjugated boronate or a MIDA boronate and that such modifications can be used during preparation of the boronates towards the final structures of use. In certain embodiments boronic acid pinacol esters are used towards the final structures and wherein the pinacol group can be readily removed by one skilled in the art. The MIDA-protected boronate esters are easily handled, stable under air, compatible with chromatography, and unreactive under standard anhydrous cross-coupling conditions and easily deprotected at room temperature under mild aqueous basic conditions using either 1M NaOH, or even $NaHCO_3$ or as described by Lee, S. J. et al. J. Am. Chem. Soc. 2008, 130, 466.

The biological mechanism by which wild type insulin binds to the insulin receptor requires rotation of the C-terminus of B-chain as previously reported. How insulin engages its primary binding site on the insulin receptor. Nature 493, 241-245 (2013); Menting, J. G. et al. Protective hinge in insulin opens to enable its receptor engagement. Proc. Natl. Acad. Sci. U.S.A. 111, E3395-3404 (2014). In certain embodiments, binding of glucose to one or more polymers results in a conformational change in the one or more polymers, or movement of the polymer with respect to insulin. In such embodiments, the aforementioned change in the polymer allows the C-terminus of the B-chain of insulin to rotate or move away from the insulin hormone core and thereby allow insulin to bind and activate the insulin receptor. In such manner certain modified insulins described herein can be responsive to glucose. It is only when glucose binds to majority of the glucose-binding agents in the modified insulin then the C-terminus of B-chain of insulin can rotate and thereby allow insulin to bind and activate the insulin receptor. One skilled in the art would recognize that changes in insulin A-chain and B-chain conformations can be determined by previously reported approaches such as X-ray protein crystallography. Glucose responsiveness can be measured for example, but not limited to, using in vitro insulin receptor binding with TyrA14-$^{125}$I human insulin as tracer and utilizing antibody binding beads with an insulin receptor monoclonal antibody. Alternatively, STZ mouse or rat models can be used for in vivo assessment of insulin activity during glucose challenge using methods that are known to one skilled in the art.

Processes for expression of insulin in *E. coli* are known and can be easily performed by one skilled in the art for using the procedures outlined in Jonasson, Eur. J. Biochem. 236:656-661 (1996); Cowley, FEBS Lett. 402:124-130 (1997); Cho, Biotechnol. Bioprocess Eng. 6: 144-149 (2001); Tikhonov, Protein Exp. Pur. 21: 176-182 (2001); Malik, Protein Exp. Pur 55: 100-111 (2007); Min, J. Biotech. 151:350-356 (2011)). In the most common process, the protein is expressed as a single-chain proinsulin construct with a fission protein or affinity tag. This approach provides good yield and reduces experimental complexity by decreasing the number of processing steps and allows refolding in a native-like insulin, see for example, Jonasson, Eur. J. Biochem. 236:656-661 (1996); Cho, Biotechnol Bioprocess Eng. 6: 144-149 (2001); Tikhonov, Protein Exp. Pur. 21: 176-182 (2001); Min, J. Biotech. 151:350-356 (2011)). When expressed in *E. coli*, proinsulin is usually found in inclusion bodies and can be easily purified by one skilled in the art.

In some embodiments the conjugates containing modified insulin may be formulated for injection. For example, it may be formulated for injection into a subject, such as a human, the composition may be a pharmaceutical composition, such as a sterile, injectable pharmaceutical composition. The composition may be formulated for subcutaneous injection.

In some embodiments, the composition is formulated for transdermal, intradermal, transmucosal, nasal, inhalable or intramuscular administration. The composition may be formulated in an oral dosage form or a pulmonary dosage form. Pharmaceutical compositions suitable for injection may include sterile aqueous solutions containing for example, sugars, polyalcohols such as mannitol and sorbitol, sodium chloride and dispersions may be prepared in glycerol, liquid polyethylene glycols, and mixtures thereof and in oils and the carrier can for example be a solvent or dispersion medium containing, for example, water, saccharides, ethanol, polyol (for example, glycerol, propylene glycol, and liquid polyethylene glycol, and the like), and suitable mixtures thereof. One skilled in the art recognizes that specific formulations can be developed to best suit the application and method of use of the modified insulins of the invention. General considerations in the formulation and manufacture of pharmaceutical compositions, routes of administrating and including suitable pharmaceutically acceptable carriers may be found, for example, in Remington's Pharmaceutical Sciences, 19th ed., Mack Publishing Co., Easton, Pa., 1995. In certain embodiments the pharmaceutical composition may include zinc, i.e., Zn2+ as for example described in U.S. Pat. No. 9,034,818. For example, the pharmaceutical composition may comprise zinc at a molar ratio to the modified insulin of about M:N where M is 1-11 and N is 6-1. Alternatively, one skilled in the art recognizes that the modified insulins may be stored in a pump, and that pump being either external or internal to the body releases the modified insulins. In certain cases, a pump may be used to release a constant amount of modified insulins wherein the insulin is glucose responsive and can automatically adjust activity based on the levels of glucose in the blood. In certain cases, the compositions may be formulated in dosage unit form for ease of administration and uniformity of dosage. In certain cases, the pharmaceutical composition may further comprise a second insulin type which provides fast-acting or basal-insulin in addition to modified insulins described herein.

In another aspect the present disclosure includes kits wherein the kit includes modified insulin as well as a pharmaceutically acceptable carrier and for injections may include a syringe or pen. In various embodiments, a kit may include a syringe or pen which is pre-filled with a pharmaceutical composition that includes the conjugate with a liquid carrier. Alternatively, a kit may include a separate container such as a vial with a pharmaceutical composition that includes the conjugate with a dry carrier and an empty syringe or pen. In certain embodiments, such a kit may include a separate container which has a liquid carrier that can be used to reconstitute a given composition that can then be taken up into the syringe or pen. In certain embodiments, a kit may include instructions. In certain embodiments the kit may include blood glucose measuring devices which either locally or remotely calculate an appropriate dose of the modified insulin that is to be injected at a given point in time, or at regular intervals. Such a dosing regimen is unique to the patient and may, for example, be provided as instruction to program a pump either by a person or by a computer. The kit may include an electronic device which transfers blood glucose measurements to a second computer, either locally or elsewhere (for example, in the cloud) which then calculate the correct amount of modified insulin that needs to be used by the patient at a certain time.

In some aspects, the invention relates to a method for treating a disease or condition in a subject, comprising administering to the subject a composition comprising a modified insulin described herein. In certain cases, the disease or condition may be hyperglycemia, type 2 diabetes, impaired glucose tolerance, type 1 diabetes, obesity, metabolic syndrome X, or dyslipidemia, diabetes during pregnancy, pre-diabetes, Alzheimer's disease, MODY 1, MODY 2 or MODY 3 diabetes. It will be appreciated that this combination approach may also be used with insulin resistant patients who are receiving an insulin sensitizer or a secondary drug for diabetes (such as, for example, a biguanide such as metformin, a glitazone) or/and an insulin secretagogue (such as, for example, a sulfonylurea, GLP-1, exendin-4 etc. . . . ) or amylin.

A conjugate of the present disclosure may be administered to a patient who is receiving at least one additional therapy or taking at least one additional drug or therapeutic protein. The at least one additional therapy is intended to treat the same disease or disorder as the administered modified insulin. In some embodiments, the at least one additional therapy is intended to treat a side-effect of insulin. The timeframe of the two therapies may differ or be the same, they may be administered on the same or different schedules as long as there is a period when the patient is receiving a benefit from both therapies. The two or more therapies may be administered within the same or different formulations as long as there is a period when the patient is receiving a benefit from both therapies. Any of these approaches may be used to administer more than one anti-diabetic drug to a subject.

In most embodiments a therapeutically effective amount of the modified insulin, which is sufficient amount of the insulin to treat (meaning for example to ameliorate the symptoms of, delay progression of, prevent recurrence of, delay onset of) the disease or condition at a reasonable benefit to risk ratio will be used. This may involve balancing of the efficacy and additional safety to toxicity. By additional safety for example, it is meant that the modified insulin can be responsive to changes in blood glucose levels even when the patient is not actively monitoring the blood glucose levels at a given timeframe, for example during sleep. In general, therapeutic efficacy and toxicity may be determined by standard pharmacological procedures in cell cultures or in vivo with experimental animals, and for example measuring $ED_{50}$ and $LD_{50}$ for therapeutic index of the drug. In various embodiments, the average daily dose of insulin is in the range of 5 to 400 U, (for example 30-150 U where 1 Unit of insulin is about 0.04 mg). In certain embodiments, an amount of conjugate with these insulin doses is administered on a daily basis or by bi-daily basis or by every three days or by every 4 days. In certain embodiments the basis is determined by an algorithm which can be computed by a computer. In certain embodiments, an amount of conjugate with 5 to 10 times these insulin doses is administered on a weekly basis or at regular intervals. In certain embodiments, an amount of conjugate with 10 to 20 times these insulin doses is administered on a bi-weekly basis or at regular intervals. In certain embodiments, an amount of conjugate with 20 to 40 times these insulin doses is administered on a monthly basis.

EXAMPLES

Example 1

Glucose-binding will be measured using competition with alizarin at different glucose concentrations in the mM range. Glucose responsiveness will be measured in vitro using insulin receptor binding with TyrA14-125I human insulin as tracer and utilizing antibody binding beads with an insulin receptor monoclonal antibody, such antibody binding beads and insulin receptor monoclonal antibodies which are readily available commercially. Solution aggregation of modified insulins will be measured using circular dichroism (CD) and using thioflavin T assay to test for aggregate formation as is known in the art. In vitro toxicity of modified insulins will be preliminarily determined using XTT or MTT assays and by measuring caspase activation. In vitro cell-based functional assays for insulin will be performed, for example, using a commercially available Glut4-EGFP redistribution assay (cytoplasmic vesicle localization) at different concentrations of glucose.

Example 2

PEGs can be readily attached to the one or more polymers or insulin through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues will also be used as a reactive group for attaching the PEGs. PEGs will be covalently attached to an amino group, especially the free amino group found in lysine residues. Numerous methods for directly attaching PEGs to proteins are described for example by in Bioconjugate Techniques (Third edition), edited by Greg T. Hermanson, Academic Press, Boston, 2013. A skilled person will recognize that various PEGylation approaches are possible.

Example 3

For this example, unless specifically indicated, the reactions were carried out at 1 ml scale.

Synthesis of Azidohomoalanine

The artificial amino acid azidohomoalanine is synthesized by copper-catalyzed diazo transfer. First 5.27 g (81.1 mmol) of sodium azide is treated with 2.7 ml (16 mmol) of distilled triflic anhydride in 13 ml of water for 2 hours. The triflic azide product is extracted with 10 ml methylene chloride and added dropwise to a flask containing Boc-protected diaminobutyric acid (Boc-Dab) (CAS #25691-37-6)(8.1 mmol), $K_2CO_3$ (1.68 g, 12.2 mmol) and $CuSO_4$ (20 mg, 0.08 mmol) in 26 ml of water and 250 ml of methanol. After 20 hours at room temperature the product is extracted with ethylacetate, redissolved in methylene chloride and purified by silica gel chromatography. After Boc deprotection with hydrochloric acid, the final product is purified by cation exchange chromatography. Azidohomoalanine is dissolved in water at a stock concentration of 100 mM and the solution is sterile filtered.

Recombinant Expression of DesB30MazideInsulin in Proinsulin Form

The DNA sequence comprising of the following coding sequence for desB30 pro-insulin: atgcgcggcagccatcatcatcat-catcatcgctttgtgaaccagcatctgtgcggcagccatctggtg-gaagcgctgtatctggtgtgcg gcgaacgcggcttttttataccaaacc-gatgcgccgcgaagcggaagatctgcaggtgggccaggtggaactgggcggc ggcccgg gcgcgggcagcctgcagccgctggcgctg-gaaggcagcctgcaggcgcgcggcattgtggaacagtgctgcaccagcat-ttgcagc ctgtatcagctggaaaactattgcggc (SEQ ID NO:9) is inserted into the pQE80Kan expression vector using standard cloning and molecular biology techniques to yield the expression vector pQE80Ins. The resulting vector is then transformed into chemically competent BL21 E. coli strain and selected for using kanamycin resistance. SEQ ID NO:9 contains a methionine codon (ATG) that codes for a methionine at position B29 of the insulin B-chain. Once expressed this DNA codes for a protein with the amino acid sequence: MRGSHHHHHHRFVNQHLCGSHLVEALYL-VCGERGFFYTKPMRREAEDLQVGQVELG GGP-GAGSLQPLALEGSLQARGIVEQCCTSICSLYQLE-NYCG (SEQ ID NO: 10) which corresponds to the pro-insulin form. When this sequence is expressed in media containing methionine then a methionine is inserted at B29. To introduce the methionine surrogate artificial amino acid azidohomoalanine at this methionine position a media replacement procedure is performed as follows. Overnight LB cultures of containing pQE80Ins are inoculated into 1 L M9 minimal media and grown to OD600 of 1 with shaking at 37° C. and then the cells are peletted and washed with M9 media and resuspended in M9 media depleted of methionine of supplemented with azidohomoalanine. IPTG is added at final concentration of 1 mM to induce expression of the pro-insulin sequence and expression is carried out at 26° C. for 4 hours and thereafter the cells are pelleted and frozen at −80° C.

Preparation of DesB30MazideInsulin

After expression of proinsulin form of DesB30MazideInsulin, cells are lysed and inclusion bodies containing the proinsulin chains are isolated and dissolved in 8M Urea. Cell lysis and isolation of inclusion bodies are readily performed by one skilled in the art. Thereafter the soluabilized proinsulin chains are isolated from remaining cellular debris through Ni-NTA affinity chromatography and purified using the polyhistidine tag that is at the N-terminus of the pro-insulin chain and the final product is dialyzed against water and lyophilized. The correct molecular weight of this expressed polypeptide which is approximately 10.7 kDa is verified by SDS polyacrylamide gel electrophoresis and MALDI-TOF mass spectrometry. The proinsulin is refolded using standard reducing solutions and sulfitolysis which is known to one skilled in the art. Next the refolded proinsulin is enzymatically digested by trypsin and carboxypeptidase enzymes which remove the leader sequence and the c-peptide portions from the proinsulin chain resulting in DesB30MazideInsulin in which the B-chain sequence is FVNQHLCGSHLVEALYLVCGERGFFYTKPX (SEQ ID NO: 11) where X is azidohomoalanine and the resulting insulin is DesB30MazideInsulin. In general, X can be inserted at any and multiple positions in insulin providing unique sites of azidohomalanine incorporation. An identical procedure can be used for introduction of certain methionine surrogate artificial amino acids containing a terminal alkyne group wherein the methionine surrogate artificial amino acid of interest is added to the expression medium instead in place of methionine and the same procedure is followed.

APP Peptide Synthesis and Linking With DesB30MazideInsulin

The one or more polymer in this case is alkyne peptide polymer (APP). Alkyne peptide polymer (APP) is first prepared from BOC protected amino acids and synthesized on a Tentagel solid support. APP with the amino acid sequence (HPG)-EGEGEEKEGEGEEKEGEGEEKEG-EGEEKGEGEE (SEQ ID NO: 12) where HPG represent the artificial amino acid homopropargylglycine (CAS #98891-36-2) is synthesized, the final peptide is HPLC purified and lyophilized. The molecular weight of the APP peptide is verified by MALDI-TOF mass spectrometry. Next, APP peptide is dissolved to a final concentration of 0.25 mg/ml in PBS pH 7.2 and sonicated to completely dissolve the powder.

DesB30MazideInsulin is mixed at equimolar concentration with APP in phosphate buffered saline to a final concentration of 0.25 mg/ml and the pH of the solution is adjusted to 7.4. Copper assisted 3+2 cycloaddition reaction, otherwise known as click chemistry reaction, between APP and DesB30MazideInsulin is carried out for 2 hours using a final concentration of 0.1 mM copper sulfate, 0.5 mM THPTA ligand (Mahdavi, A.; Szychowski, J.; Ngo, J. T.; Sweredoski, M. J.; Graham, R. L.; Hess, S.; Schneewind, O.;

Mazmanian, S. K.; Tirrell, D. A. Proc. Natl. Acad. Sci. U.S.A. 2014, 111, 433), 5 mM sodium ascorbate, 5 mM aminoguanidine. Copper is removed using EDTA and the conjugation of APP with DesB30MazideInsulin is verified by polyacrylamide SDS gel electrophoresis by comparing the conjugate with DesB30MazideInsulin and monitoring the approximately 4kDA shift that results from conjugation of the APP to DesB30MazideInsulin. The resulting conjugate DesB30APP is purified by HPLC and lyophilized.

Development of Glucose-Binding Agent AzidoPBA

3-Aminophenylboronic acid monohydrate (CAS #206658-89-1) is first dissolved in PBS to a final concentration of 1 mg/ml and pH adjusted to 8.4. Next 15-Azido-4,7,10,13-tetraoxapentadecanoic Acid N-Succinimidyl Ester (CAS #944251-24-5) is diluted form a DMSO stock into the solution containing 3-Aminophenylboronic acid monohydrate to a final concentration of 1 mg/ml and pH is adjusted to 8.4 and the reaction is carried out for 5 hours at room temperature and then quenched with addition of lysine to 40 mM final concentration.

Functionalization of DesB30APP

DesB30APP is dissolved in PBS pH 3.5 and the pH is slowly adjusted to 8.4 until a clear solution is obtained with a final concentration of 0.5 mg/ml DesB30APP. DBCO-PEG4-NHS ester heterobifunctional linker (CAS #1427004-19-0) which contains the reactive azadibenzocyclooctyne moiety is first dissolved in DMSO as a stock solution and then added to the solution of DesB30APP to a final concentration of 10 molar equivalents and the reaction is carried out for 5 hours at room temperature and then quenched with addition of lysine to 40 mM final concentration. The resulting product, DBCODesB30APP is next functionalized.

Functionalization of DBCODesB30APP

Decoy ligand 6-Azido-6-deoxy-D-glucose (CAS #20847-05-6) is mixed at 1:1 molar ratio with the decoy ligand 2-Azido-2-deoxy-D-glucose (CAS #56883-39-7) at a final concentration of 4 mM and this solution is then added to an equal volume of 4 mM solution of glucose-binding agent AzidoPBA. This combined solution containing 6-Azido-6-deoxy-D-glucose, 2-Azido-2-deoxy-D-glucose and AzidoPBA is then added at equal volumetric ratio to a 0.5 mg/ml solution of DBCODesB30APP and the reaction is carried out for 2 hours at room temperature to yield the final modified insulin conjugate and this serves as an example of a modified insulin conjugate. Preliminary in vitro measure of glucose responsiveness of this modified insulin conjugate is performed by incbating HEK293T cells at different concentrations of glucose and a fixed concentration of the modified insulin conjugate and then measuring the extend of insulin receptor phosphorylation of these cells using an ELISA sandwich assay utilizing a phospho-Insulin Receptor β (Tyr1150/1151) monoclonal antibody ELISA kit which is readily available commercially.

Example 4

To measure the in vivo functionality of the modified insulins as a function of glucose concentration for in vivo measurements, often performed in rodents, the following glucose clamp method can be used. Double jugular vein (JV/JV) catheterized rats are maintained at a desired target glucose value (100, 200, 300 or 400 mg/dl) for required periods of time by infusing a 50% dextrose solution through the catheter line. The target blood glucose level which is set by design and maintained at a particular level by adjusting the glucose infusion rate are followed. After the modified insulin is injected subcutaneously at given dose (U/kg), the glucose infusion rate is adjusted to compensate for the glucose lowering activity of the modified insulin. Blood glucose levels are measured by tail vein bleeding and the glucose infusion rate is varied to compensate for any drift. The glucose infusion rate required to maintain the glucose levels at a given target concentration provides a measure of the activity of the modified insulin at that given glucose concentration. In general, a higher glucose infusion rate should be observed (when compared to wild type insulin) at target glucose concentrations of 300-400 mg/dL which would indicate the functionality of the modified insulin. Additionally, lower glucose concentrations can be tested.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. An insulin molecule comprising insulin, an insulin analogue, glucagon, GLP-1, GLP-2, or a GLP-1 agonist, the insulin molecule containing one or more artificial amino acids independently selected from F26-F41:

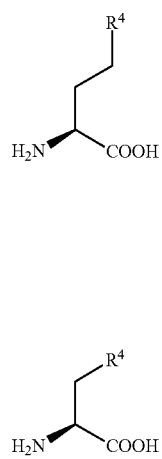

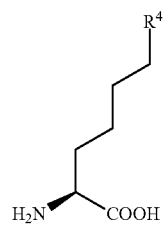

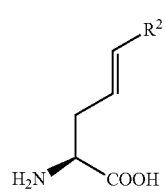

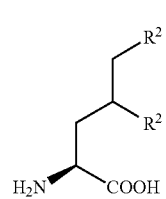

-continued

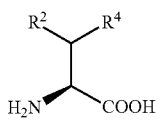

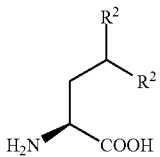

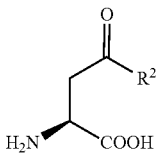

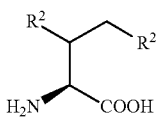

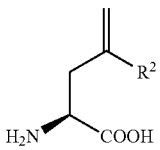

F36
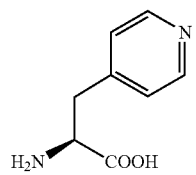

F37
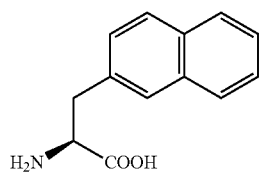

F38
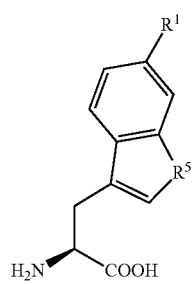

F39
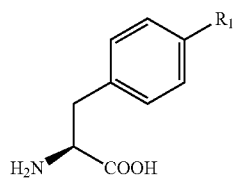

-continued

F31

F32

F33

F34

F35

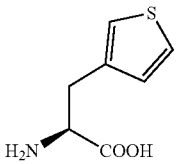 F40

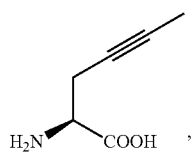 F41 wherein:

each $R^1$ is independently selected from —H, —NH$_2$, —NO$_2$, —Cl, —CF$_3$, —I, —COCH$_3$, —CN, —C≡CH, —N$_3$, or —Br, each $R^2$ is independently selected from —CF$_3$, —H, or —CH$_3$;

each $R^3$ is independently selected from —C≡CH, —H, —N$_3$, or vinyl group;

each $R^4$ is independently selected from $R^2$ or $R^3$, each $R^5$ is independently selected from —S— or —NH—; and wherein if $R^1$ or $R^3$ is —N$_3$ the one or more artificial amino acids is independently covalently conjugated using click chemistry to an alkyne functional group, and if $R^1$ or $R^3$ is —C≡CH the one or more artificial amino acids is independently covalently conjugated using click chemistry to a terminal azide functional group, or alternatively $R^1$, $R^2$, $R^3$, $R^4$, or $R^5$ is independently covalently conjugated using native chemical ligation, biorthogonal reactions, click chemistry, cycloaddition reactions, strain-promoted Alkyne-Nitrone Cycloadditions, Strained Alkenes, Alkene and Tetrazine inverse-demand Diels-Alder, Copper (I)-Catalyzed Azide-Alkyne Cycloaddition (CuAAC), Strain-promoted Azide-Alkyne Cycloaddition, Staudinger ligation, nucleophilic ring-opening reaction or additions to carbon-carbon multiple bonds.

2. The insulin molecule of claim 1, wherein each of the one or more artificial amino acids is independently covalently conjugated, either directly or through a linker, to one selected from: a side chain of a lysine, and an N-terminus of the insulin molecule.

3. The insulin molecule of claim 2, wherein one or more polypeptides are inserted into, and/or covalently conjugated to, the sequence of insulin, and wherein each polypeptide independently comprises a subset of amino acids E, G, K, S, C, and X, wherein X is A, P, Q, and each K is covalently conjugated to one of the one or more artificial amino acids.

4. The insulin molecule of claim 2, wherein the linker comprises one or more covalently conjugated amino acids selected from natural amino acids, an L or D artificial amino acid, or a β-amino acid.

5. The insulin molecule of claim 2, wherein each of the one or more artificial amino acids is independently boronate functionalized or covalently conjugated to one or more chemical structures described by Formula F3 or Formula F4:

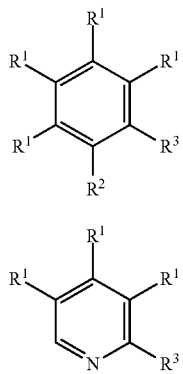

wherein:
each $R^1$ is independently selected from —H, —F, —Cl, —CH$_3$, —B(OH)$_2$, —C≡N, —NO$_2$, or —R$^4$,
each $R^2$ is independently selected from —H, —C≡N, —(SO$_2$)NH(R$^4$), or —R$^4$,
each $R^3$ is independently selected from —C≡N, —CONH(R$^4$), —NH(R$^4$), —(SO$_2$)NH(R$^4$), or —R$^4$,
each $R^4$ is independently selected from —H, —N$_3$, —C≡CH, —CH$_2$N(R$^5$) or a linker, and
each $R^5$ is independently selected from —H or a linker, and
wherein at least one of the $R^1$ is —B(OH)$_2$.

6. The insulin molecule of claim 5, wherein the linker in F3 or F4 covalently conjugates F3 or F4 to the artificial amino acid.

7. The insulin molecule of claim 5, wherein one $R^1$ is $R^4$, and $R^4$ is the linker that covalently conjugates F3 or F4 to the artificial amino acid.

8. The insulin molecule of claim 2, wherein each of the one or more artificial amino acids is independently boronate functionalized or covalently conjugated to one or more chemical structures described by Formula F3 or Formula F4:

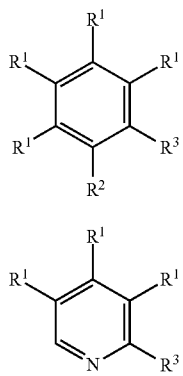

wherein for each of Formulae F3 and F4:
each $R^1$ is independently selected from —H, —F, —Cl, —CH$_3$, —CH$_2$OH, —B(OH)$_2$, —C≡N, —NO$_2$, or —R$^4$,
each $R^2$ is independently selected from —H, —C≡N, —(SO$_2$)NH(R$^4$), or —R$^4$,
each $R^3$ is independently selected from —C≡N, —CONH(R$^4$), —NH(R$^4$), —(SO$_2$)NH(R$^4$), or —R$^4$,
each $R^4$ is independently selected from —H, —N$_3$, —C≡CH, —CH$_2$N(R$^5$) or a linker,
each $R^5$ is independently selected from —H or a linker, and
wherein at least one of the $R^1$ is —B(OH)$_2$;
wherein when $R^1$ or $R^3$ is —N$_3$ in F26-F28, then the covalent conjugation between one of the boronate-functionalized groups, F3, or F4, and the artificial amino acid, is via a Staudinger ligation.

9. The insulin molecule of claim 2, wherein the one or more artificial amino acids is each independently covalently conjugated to at least one boronate ester, boronate, boronic acid, or phenylboronic acid or an analog thereof.

10. The insulin molecule of claim 1, wherein one or more polypeptides are inserted into, and/or covalently conjugated to, the sequence of insulin, and wherein each of the one or more polypeptides independently comprises a subset of amino acids E, G, K, S, C, and X, wherein X is A, P, Q, and each K is covalently conjugated to one of the one or more artificial amino acids.

11. The insulin molecule of claim 1, wherein the one or more artificial amino acids is each independently covalently conjugated to at least one boronate ester, boronate, boronic acid, or phenylboronic acid or an analog thereof.

12. The insulin molecule of claim 1, wherein each of the one or more artificial amino acids is independently boronate functionalized or covalently conjugated to one or more chemical structures described by Formula F3 or Formula F4:

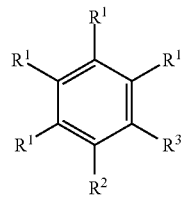

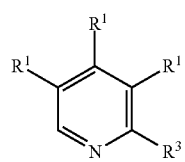

wherein:
each $R^1$ is independently selected from —H, —F, —Cl, —CH$_3$, —B(OH)$_2$, —C≡N, —NO$_2$, or —R$^4$,
each $R^2$ is independently selected from —H, —C≡N, —(SO$_2$)NH(R$^4$), or —R$^4$,
each $R^3$ is independently selected from —C≡N, —CONH(R$^4$), —NH(R$^4$), —(SO$_2$)NH(R$^4$), or —R$^4$,
each $R^4$ is independently selected from —H, —N$_3$, —C≡CH, —CH$_2$N(R$^5$) or a linker, and
each $R^5$ is independently selected from —H or a linker, and
wherein at least one of the $R^1$ is —B(OH)$_2$.

13. The insulin molecule of claim 12, wherein the linker in F3 or F4 covalently conjugates F3 or F4 to the artificial amino acid.

14. The insulin molecule of claim 12, wherein one $R^1$ is $R^4$, and $R^4$ is the linker that covalently conjugates F3 or F4 to the artificial amino acid.

15. The insulin molecule of claim 1, wherein each of the one or more artificial amino acids is independently boronate functionalized or covalently conjugated to one or more chemical structures described by Formula F3 or Formula F4:

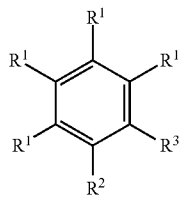

wherein for each of Formulae F3 and F4:
each $R^1$ is independently selected from —H, —F, —Cl, —$CH_3$, —$CH_2OH$, —$B(OH)_2$, —C≡N, —$NO_2$, or —$R^4$,
each $R^2$ is independently selected from —H, —C≡N, —$(SO_2)NH(R^4)$, or —$R^4$,
each $R^3$ is independently selected from —C≡N, —$CONH(R^4)$, —$NH(R^4)$, —$(SO_2)NH(R^4)$, or —$R^4$,
each $R^4$ is independently selected from —H, —$N_3$, —C≡CH, —$CH_2N(R^5)$ or a linker,
each $R^5$ is independently selected from —H or a linker, and
wherein at least one of the $R^1$ is —$B(OH)_2$;
wherein when $R^1$ or $R^3$ is —$N_3$ in F26-F28, then the covalent conjugation between one of the boronate-functionalized groups, F3, or F4, and the artificial amino acid, is via a Staudinger ligation.

\* \* \* \* \*

SEQUENCE LISTING

```
<160> NUMBER OF SEQ ID NOS: 20

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

-continued

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
```

|     |     |     |     |     | 485 |     |     |     | 490 |     |     |     |     | 495 |
| --- | --- | --- | --- | --- | --- | --- | --- | --- | --- | --- | --- | --- | --- | --- |

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
                20                  25                  30

<210> SEQ ID NO 4
<211> LENGTH: 465
<212> TYPE: PRT
<213> ORGANISM: Homo sapiens

<400> SEQUENCE: 4

Met Leu Asp Asp Arg Ala Arg Met Glu Ala Ala Lys Lys Glu Lys Val
1               5                   10                  15

Glu Gln Ile Leu Ala Glu Phe Gln Leu Gln Glu Glu Asp Leu Lys Lys
                20                  25                  30

Val Met Arg Arg Met Gln Lys Glu Met Asp Arg Gly Leu Arg Leu Glu
                35                  40                  45

Thr His Glu Glu Ala Ser Val Lys Met Leu Pro Thr Tyr Val Arg Ser
                50                  55                  60

Thr Pro Glu Gly Ser Glu Val Gly Asp Phe Leu Ser Leu Asp Leu Gly
65              70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
            245                 250                 255

Trp Gly Ala Phe Gly Asp Ser Gly Glu Leu Asp Glu Phe Leu Leu Glu
        260                 265                 270

Tyr Asp Arg Leu Val Asp Glu Ser Ala Asn Pro Gly Gln Gln Leu
    275                 280                 285

Tyr Glu Lys Leu Ile Gly Gly Lys Tyr Met Gly Glu Leu Val Arg Leu
            290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
        355                 360                 365

Arg Ala Cys Glu Ser Val Ser Thr Arg Ala Ala His Met Cys Ser Ala
370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
            405                 410                 415

Pro Ser Phe Lys Glu Arg Phe His Ala Ser Val Arg Arg Leu Thr Pro
        420                 425                 430

Ser Cys Glu Ile Thr Phe Ile Glu Ser Glu Glu Gly Ser Gly Arg Gly
    435                 440                 445

Ala Ala Leu Val Ser Ala Val Ala Cys Lys Lys Ala Cys Met Leu Gly
        450                 455                 460

Gln
465

<210> SEQ ID NO 5
<211> LENGTH: 917
<212> TYPE: PRT
<213> ORGANISM: Homo sapiens

<400> SEQUENCE: 5

-continued

```
Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Thr Leu Ile Asp Ile Met Thr Arg Phe Arg Lys Glu Met Lys
            35                  40                  45

Asn Gly Leu Ser Arg Asp Phe Asn Pro Thr Ala Thr Val Lys Met Leu
50                  55                  60

Pro Thr Phe Val Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val His Met Glu Ser Glu Val Tyr
                100                 105                 110

Asp Thr Pro Glu Asn Ile Val His Gly Ser Gly Ser Gln Leu Phe Asp
            115                 120                 125

His Val Ala Glu Cys Leu Gly Asp Phe Met Glu Lys Arg Lys Ile Lys
        130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
                165                 170                 175

Ala Ser Gly Val Glu Gly Ala Asp Val Val Lys Leu Leu Asn Lys Ala
                180                 185                 190

Ile Lys Lys Arg Gly Asp Tyr Asp Ala Asn Ile Val Ala Val Val Asn
            195                 200                 205

Asp Thr Val Gly Thr Met Met Thr Cys Gly Tyr Asp Asp Gln His Cys
        210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Glu Gly Arg Met Cys
                245                 250                 255

Ile Asn Thr Glu Trp Gly Ala Phe Gly Asp Asp Gly Ser Leu Glu Asp
                260                 265                 270

Ile Arg Thr Glu Phe Asp Arg Glu Ile Asp Arg Gly Ser Leu Asn Pro
            275                 280                 285

Gly Lys Gln Leu Phe Glu Lys Met Val Ser Gly Met Tyr Leu Gly Glu
290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
            340                 345                 350

Lys Glu Ile Leu Thr Arg Leu Gly Val Glu Pro Ser Asp Asp Cys
        355                 360                 365

Val Ser Val Gln His Val Cys Thr Ile Val Ser Phe Arg Ser Ala Asn
370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415
```

```
Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
            435                 440                 445

Ser Gly Lys Gly Ala Ala Met Val Thr Ala Val Ala Tyr Arg Leu Ala
        450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495

Leu Gly Leu Arg Lys Gln Thr His Asn Asn Ala Val Val Lys Met Leu
            500                 505                 510

Pro Ser Phe Val Arg Arg Thr Pro Asp Gly Thr Glu Asn Gly Asp Phe
            515                 520                 525

Leu Ala Leu Asp Leu Gly Gly Thr Asn Phe Arg Val Leu Leu Val Lys
        530                 535                 540

Ile Arg Ser Gly Lys Lys Arg Thr Val Glu Met His Asn Lys Ile Tyr
545                 550                 555                 560

Ala Ile Pro Ile Glu Ile Met Gln Gly Thr Gly Glu Glu Leu Phe Asp
                565                 570                 575

His Ile Val Ser Cys Ile Ser Asp Phe Leu Asp Tyr Met Gly Ile Lys
            580                 585                 590

Gly Pro Arg Met Pro Leu Gly Phe Thr Phe Ser Phe Pro Cys Gln Gln
        595                 600                 605

Thr Ser Leu Asp Ala Gly Ile Leu Ile Thr Trp Thr Lys Gly Phe Lys
610                 615                 620

Ala Thr Asp Cys Val Gly His Asp Val Val Thr Leu Leu Arg Asp Ala
625                 630                 635                 640

Ile Lys Arg Arg Glu Glu Phe Asp Leu Asp Val Val Ala Val Val Asn
                645                 650                 655

Asp Thr Val Gly Thr Met Met Thr Cys Ala Tyr Glu Glu Pro Thr Cys
            660                 665                 670

Glu Val Gly Leu Ile Val Gly Thr Gly Ser Asn Ala Cys Tyr Met Glu
        675                 680                 685

Glu Met Lys Asn Val Glu Met Val Glu Gly Asp Gln Gly Gln Met Cys
690                 695                 700

Ile Asn Met Glu Trp Gly Ala Phe Gly Asp Asn Gly Cys Leu Asp Asp
705                 710                 715                 720

Ile Arg Thr His Tyr Asp Arg Leu Val Asp Glu Tyr Ser Leu Asn Ala
                725                 730                 735

Gly Lys Gln Arg Tyr Glu Lys Met Ile Ser Gly Met Tyr Leu Gly Glu
            740                 745                 750

Ile Val Arg Asn Ile Leu Ile Asp Phe Thr Lys Lys Gly Phe Leu Phe
        755                 760                 765

Arg Gly Gln Ile Ser Glu Thr Leu Lys Thr Arg Gly Ile Phe Glu Thr
770                 775                 780

Lys Phe Leu Ser Gln Ile Glu Ser Asp Arg Leu Ala Leu Leu Gln Val
785                 790                 795                 800

Arg Ala Ile Leu Gln Gln Leu Gly Leu Asn Ser Thr Cys Asp Asp Ser
                805                 810                 815

Ile Leu Val Lys Thr Val Cys Gly Val Val Ser Arg Arg Ala Ala Gln
            820                 825                 830

Leu Cys Gly Ala Gly Met Ala Ala Val Val Asp Lys Ile Arg Glu Asn
```

```
                      835                 840                 845

Arg Gly Leu Asp Arg Leu Asn Val Thr Val Gly Val Asp Gly Thr Leu
    850                 855                 860

Tyr Lys Leu His Pro His Phe Ser Arg Ile Met His Gln Thr Val Lys
865                 870                 875                 880

Glu Leu Ser Pro Lys Cys Asn Val Ser Phe Leu Leu Ser Glu Asp Gly
                    885                 890                 895

Ser Gly Lys Gly Ala Ala Leu Ile Thr Ala Val Gly Val Arg Leu Arg
                900                 905                 910

Thr Glu Ala Ser Ser
        915

<210> SEQ ID NO 6
<211> LENGTH: 917
<212> TYPE: PRT
<213> ORGANISM: Homo sapiens

<400> SEQUENCE: 6

Met Ile Ala Ser His Leu Leu Ala Tyr Phe Phe Thr Glu Leu Asn His
1               5                   10                  15

Asp Gln Val Gln Lys Val Asp Gln Tyr Leu Tyr His Met Arg Leu Ser
            20                  25                  30

Asp Glu Thr Leu Leu Glu Ile Ser Lys Arg Phe Arg Lys Glu Met Glu
        35                  40                  45

Lys Gly Leu Gly Ala Thr Thr His Pro Thr Ala Ala Val Lys Met Leu
    50                  55                  60

Pro Thr Phe Val Arg Ser Thr Pro Asp Gly Thr Glu His Gly Glu Phe
65                  70                  75                  80

Leu Ala Leu Asp Leu Gly Gly Thr Asn Phe Arg Val Leu Trp Val Lys
                85                  90                  95

Val Thr Asp Asn Gly Leu Gln Lys Val Glu Met Glu Asn Gln Ile Tyr
            100                 105                 110

Ala Ile Pro Glu Asp Ile Met Arg Gly Ser Gly Thr Gln Leu Phe Asp
        115                 120                 125

His Ile Ala Glu Cys Leu Ala Asn Phe Met Asp Lys Leu Gln Ile Lys
    130                 135                 140

Asp Lys Lys Leu Pro Leu Gly Phe Thr Phe Ser Phe Pro Cys His Gln
145                 150                 155                 160

Thr Lys Leu Asp Glu Ser Phe Leu Val Ser Trp Thr Lys Gly Phe Lys
                165                 170                 175

Ser Ser Gly Val Glu Gly Arg Asp Val Val Ala Leu Ile Arg Lys Ala
            180                 185                 190

Ile Gln Arg Arg Gly Asp Phe Asp Ile Asp Ile Val Ala Val Val Asn
        195                 200                 205

Asp Thr Val Gly Thr Met Met Thr Cys Gly Tyr Asp Asp His Asn Cys
    210                 215                 220

Glu Ile Gly Leu Ile Val Gly Thr Gly Ser Asn Ala Cys Tyr Met Glu
225                 230                 235                 240

Glu Met Arg His Ile Asp Met Val Glu Gly Asp Glu Gly Arg Met Cys
                245                 250                 255

Ile Asn Met Glu Trp Gly Ala Phe Gly Asp Asp Gly Ser Leu Asn Asp
            260                 265                 270

Ile Arg Thr Glu Phe Asp Gln Glu Ile Asp Met Gly Ser Leu Asn Pro
        275                 280                 285
```

```
Gly Lys Gln Leu Phe Glu Lys Met Ile Ser Gly Met Tyr Met Gly Glu
290                 295                 300

Leu Val Arg Leu Ile Leu Val Lys Met Ala Lys Glu Glu Leu Leu Phe
305                 310                 315                 320

Gly Gly Lys Leu Ser Pro Glu Leu Leu Asn Thr Gly Arg Phe Glu Thr
                325                 330                 335

Lys Asp Ile Ser Asp Ile Glu Gly Glu Lys Asp Gly Ile Arg Lys Ala
                340                 345                 350

Arg Glu Val Leu Met Arg Leu Gly Leu Asp Pro Thr Gln Glu Asp Cys
                355                 360                 365

Val Ala Thr His Arg Ile Cys Gln Ile Val Ser Thr Arg Ser Ala Ser
370                 375                 380

Leu Cys Ala Ala Thr Leu Ala Ala Val Leu Gln Arg Ile Lys Glu Asn
385                 390                 395                 400

Lys Gly Glu Glu Arg Leu Arg Ser Thr Ile Gly Val Asp Gly Ser Val
                405                 410                 415

Tyr Lys Lys His Pro His Phe Ala Lys Arg Leu His Lys Thr Val Arg
                420                 425                 430

Arg Leu Val Pro Gly Cys Asp Val Arg Phe Leu Arg Ser Glu Asp Gly
                435                 440                 445

Ser Gly Lys Gly Ala Ala Met Val Thr Ala Val Ala Tyr Arg Leu Ala
                450                 455                 460

Asp Gln His Arg Ala Arg Gln Lys Thr Leu Glu His Leu Gln Leu Ser
465                 470                 475                 480

His Asp Gln Leu Leu Glu Val Lys Arg Arg Met Lys Val Glu Met Glu
                485                 490                 495

Arg Gly Leu Ser Lys Glu Thr His Ala Ser Ala Pro Val Lys Met Leu
                500                 505                 510

Pro Thr Tyr Val Cys Ala Thr Pro Asp Gly Thr Glu Lys Gly Asp Phe
                515                 520                 525

Leu Ala Leu Asp Leu Gly Gly Thr Asn Phe Arg Val Leu Leu Val Arg
530                 535                 540

Val Arg Asn Gly Lys Trp Gly Gly Val Glu Met His Asn Lys Ile Tyr
545                 550                 555                 560

Ala Ile Pro Gln Glu Val Met His Gly Thr Gly Asp Glu Leu Phe Asp
                565                 570                 575

His Ile Val Gln Cys Ile Ala Asp Phe Leu Glu Tyr Met Gly Met Lys
                580                 585                 590

Gly Val Ser Leu Pro Leu Gly Phe Thr Phe Ser Phe Pro Cys Gln Gln
                595                 600                 605

Asn Ser Leu Asp Glu Ser Ile Leu Leu Lys Trp Thr Lys Gly Phe Lys
                610                 615                 620

Ala Ser Gly Cys Glu Gly Glu Asp Val Val Thr Leu Leu Lys Glu Ala
625                 630                 635                 640

Ile His Arg Arg Glu Glu Phe Asp Leu Asp Val Val Ala Val Val Asn
                645                 650                 655

Asp Thr Val Gly Thr Met Met Thr Cys Gly Phe Glu Asp Pro His Cys
                660                 665                 670

Glu Val Gly Leu Ile Val Gly Thr Gly Ser Asn Ala Cys Tyr Met Glu
                675                 680                 685

Glu Met Arg Asn Val Glu Leu Val Glu Gly Glu Glu Gly Arg Met Cys
                690                 695                 700

Val Asn Met Glu Trp Gly Ala Phe Gly Asp Asn Gly Cys Leu Asp Asp
```

-continued

```
            705                 710                 715                 720
        Phe Arg Thr Glu Phe Asp Val Ala Val Asp Glu Leu Ser Leu Asn Pro
                        725                 730                 735
        Gly Lys Gln Arg Phe Glu Lys Met Ile Ser Gly Met Tyr Leu Gly Glu
                        740                 745                 750
        Ile Val Arg Asn Ile Leu Ile Asp Phe Thr Lys Arg Gly Leu Leu Phe
                        755                 760                 765
        Arg Gly Arg Ile Ser Glu Arg Leu Lys Thr Arg Gly Ile Phe Glu Thr
                        770                 775                 780
        Lys Phe Leu Ser Gln Ile Glu Ser Asp Cys Leu Ala Leu Leu Gln Val
        785                 790                 795                 800
        Arg Ala Ile Leu Gln His Leu Gly Leu Glu Ser Thr Cys Asp Asp Ser
                        805                 810                 815
        Ile Ile Val Lys Glu Val Cys Thr Val Ala Arg Arg Ala Ala Gln
                        820                 825                 830
        Leu Cys Gly Ala Gly Met Ala Ala Val Asp Arg Ile Arg Glu Asn
                        835                 840                 845
        Arg Gly Leu Asp Ala Leu Lys Val Thr Val Gly Val Asp Gly Thr Leu
        850                 855                 860
        Tyr Lys Leu His Pro His Phe Ala Lys Val Met His Glu Thr Val Lys
        865                 870                 875                 880
        Asp Leu Ala Pro Lys Cys Asp Val Ser Phe Leu Gln Ser Glu Asp Gly
                        885                 890                 895
        Ser Gly Lys Gly Ala Ala Leu Ile Thr Ala Val Ala Cys Arg Ile Arg
                        900                 905                 910
        Glu Ala Gly Gln Arg
                        915

<210> SEQ ID NO 7
<211> LENGTH: 923
<212> TYPE: PRT
<213> ORGANISM: Homo sapiens

<400> SEQUENCE: 7

Met Asp Ser Ile Gly Ser Ser Gly Leu Arg Gln Gly Glu Glu Thr Leu
1               5                   10                  15
Ser Cys Ser Glu Glu Gly Leu Pro Gly Pro Ser Asp Ser Ser Glu Leu
                20                  25                  30
Val Gln Glu Cys Leu Gln Gln Phe Lys Val Thr Arg Ala Gln Leu Gln
                35                  40                  45
Gln Ile Gln Ala Ser Leu Leu Gly Ser Met Glu Gln Ala Leu Arg Gly
                50                  55                  60
Gln Ala Ser Pro Ala Pro Ala Val Arg Met Leu Pro Thr Tyr Val Gly
65                  70                  75                  80
Ser Thr Pro His Gly Thr Glu Gln Gly Asp Phe Val Val Leu Glu Leu
                85                  90                  95
Gly Ala Thr Gly Ala Ser Leu Arg Val Leu Trp Val Thr Leu Thr Gly
                100                 105                 110
Ile Glu Gly His Arg Val Glu Pro Arg Ser Gln Glu Phe Val Ile Pro
                115                 120                 125
Gln Glu Val Met Leu Gly Ala Gly Gln Gln Leu Phe Asp Phe Ala Ala
                130                 135                 140
His Cys Leu Ser Glu Phe Leu Asp Ala Gln Pro Val Asn Lys Gln Gly
145                 150                 155                 160
```

-continued

Leu Gln Leu Gly Phe Ser Phe Ser Phe Pro Cys His Gln Thr Gly Leu
            165                 170                 175
Asp Arg Ser Thr Leu Ile Ser Trp Thr Lys Gly Phe Arg Cys Ser Gly
            180                 185                 190
Val Glu Gly Gln Asp Val Val Gln Leu Leu Arg Asp Ala Ile Arg Arg
            195                 200                 205
Gln Gly Ala Tyr Asn Ile Asp Val Val Ala Val Val Asn Asp Thr Val
            210                 215                 220
Gly Thr Met Met Gly Cys Glu Pro Gly Val Arg Pro Cys Glu Val Gly
225                 230                 235                 240
Leu Val Val Asp Thr Gly Thr Asn Ala Cys Tyr Met Glu Glu Ala Arg
            245                 250                 255
His Val Ala Val Leu Asp Glu Asp Arg Gly Arg Val Cys Val Ser Val
            260                 265                 270
Glu Trp Gly Ser Phe Ser Asp Asp Gly Ala Leu Gly Pro Val Leu Thr
            275                 280                 285
Thr Phe Asp His Thr Leu Asp His Glu Ser Leu Asn Pro Gly Ala Gln
            290                 295                 300
Arg Phe Glu Lys Met Ile Gly Gly Leu Tyr Leu Gly Glu Leu Val Arg
305                 310                 315                 320
Leu Val Leu Ala His Leu Ala Arg Cys Gly Val Leu Phe Gly Cys
            325                 330                 335
Thr Ser Pro Ala Leu Leu Ser Gln Gly Ser Ile Leu Leu Glu His Val
            340                 345                 350
Ala Glu Met Glu Asp Pro Ser Thr Gly Ala Ala Arg Val His Ala Ile
            355                 360                 365
Leu Gln Asp Leu Gly Leu Ser Pro Gly Ala Ser Asp Val Glu Leu Val
            370                 375                 380
Gln His Val Cys Ala Ala Val Cys Thr Arg Ala Ala Gln Leu Cys Ala
385                 390                 395                 400
Ala Ala Leu Ala Ala Val Leu Ser Cys Leu Gln His Ser Arg Glu Gln
            405                 410                 415
Gln Thr Leu Gln Val Ala Val Ala Thr Gly Gly Arg Val Cys Glu Arg
            420                 425                 430
His Pro Arg Phe Cys Ser Val Leu Gln Gly Thr Val Met Leu Leu Ala
            435                 440                 445
Pro Glu Cys Asp Val Ser Leu Ile Pro Ser Val Asp Gly Gly Arg
450                 455                 460
Gly Val Ala Met Val Thr Ala Val Ala Ala Arg Leu Ala Ala His Arg
465                 470                 475                 480
Arg Leu Leu Glu Glu Thr Leu Ala Pro Phe Arg Leu Asn His Asp Gln
            485                 490                 495
Leu Ala Ala Val Gln Ala Gln Met Arg Lys Ala Met Ala Lys Gly Leu
            500                 505                 510
Arg Gly Glu Ala Ser Ser Leu Arg Met Leu Pro Thr Phe Val Arg Ala
            515                 520                 525
Thr Pro Asp Gly Ser Glu Arg Gly Asp Phe Leu Ala Leu Asp Leu Gly
            530                 535                 540
Gly Thr Asn Phe Arg Val Leu Leu Val Arg Val Thr Thr Gly Val Gln
545                 550                 555                 560
Ile Thr Ser Glu Ile Tyr Ser Ile Pro Glu Thr Val Ala Gln Gly Ser
            565                 570                 575
Gly Gln Gln Leu Phe Asp His Ile Val Asp Cys Ile Val Asp Phe Gln 580                 585                 590
Gln Lys Gln Gly Leu Ser Gly Gln Ser Leu Pro Leu Gly Phe Thr Phe
            595                 600                 605

Ser Phe Pro Cys Arg Gln Leu Gly Leu Asp Gln Gly Ile Leu Leu Asn
610                 615                 620

Trp Thr Lys Gly Phe Lys Ala Ser Asp Cys Glu Gly Gln Asp Val Val
625                 630                 635                 640

Ser Leu Leu Arg Glu Ala Ile Thr Arg Arg Gln Ala Val Glu Leu Asn
            645                 650                 655

Val Val Ala Ile Val Asn Asp Thr Val Gly Thr Met Met Ser Cys Gly
                660                 665                 670

Tyr Glu Asp Pro Arg Cys Glu Ile Gly Leu Ile Val Gly Thr Gly Thr
            675                 680                 685

Asn Ala Cys Tyr Met Glu Glu Leu Arg Asn Val Ala Gly Val Pro Gly
            690                 695                 700

Asp Ser Gly Arg Met Cys Ile Asn Met Glu Trp Gly Ala Phe Gly Asp
705                 710                 715                 720

Asp Gly Ser Leu Ala Met Leu Ser Thr Arg Phe Asp Ala Ser Val Asp
                725                 730                 735

Gln Ala Ser Ile Asn Pro Gly Lys Gln Arg Phe Glu Lys Met Ile Ser
            740                 745                 750

Gly Met Tyr Leu Gly Glu Ile Val Arg His Ile Leu Leu His Leu Thr
            755                 760                 765

Ser Leu Gly Val Leu Phe Arg Gly Gln Gln Ile Gln Arg Leu Gln Thr
770                 775                 780

Arg Asp Ile Phe Lys Thr Lys Phe Leu Ser Glu Ile Glu Ser Asp Ser
785                 790                 795                 800

Leu Ala Leu Arg Gln Val Arg Ala Ile Leu Glu Asp Leu Gly Leu Pro
                805                 810                 815

Leu Thr Ser Asp Asp Ala Leu Met Val Leu Glu Val Cys Gln Ala Val
            820                 825                 830

Ser Gln Arg Ala Ala Gln Leu Cys Gly Ala Gly Val Ala Ala Val Val
            835                 840                 845

Glu Lys Ile Arg Glu Asn Arg Gly Leu Glu Glu Leu Ala Val Ser Val
850                 855                 860

Gly Val Asp Gly Thr Leu Tyr Lys Leu His Pro Arg Phe Ser Ser Leu
865                 870                 875                 880

Val Ala Ala Thr Val Arg Glu Leu Ala Pro Arg Cys Val Val Thr Phe
                885                 890                 895

Leu Gln Ser Glu Asp Gly Ser Gly Lys Gly Ala Ala Leu Val Thr Ala
            900                 905                 910

Val Ala Cys Arg Leu Ala Gln Leu Thr Arg Val
            915                 920

<210> SEQ ID NO 8
<211> LENGTH: 5
<212> TYPE: PRT
<213> ORGANISM: Artificial Sequence
<220> FEATURE:
<223> OTHER INFORMATION: Synthetic Insert
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

-continued

```
Val Pro Gly Xaa Gly
1               5

<210> SEQ ID NO 9
<211> LENGTH: 291
<212> TYPE: PRT
<213> ORGANISM: Artificial Sequence
<220> FEATURE:
<223> OTHER INFORMATION: desB30 pro-insulin

<400> SEQUENCE: 9

Ala Thr Gly Cys Gly Cys Gly Gly Cys Ala Gly Cys Ala Thr Cys
1               5                   10                  15

Ala Thr Cys Ala Thr Cys Ala Thr Cys Ala Thr Cys Ala Thr Gly
                20                  25                  30

Cys Thr Thr Thr Gly Thr Gly Ala Ala Cys Cys Ala Gly Cys Ala Thr
                35                  40                  45

Cys Thr Gly Thr Gly Cys Gly Gly Cys Ala Gly Cys Cys Ala Thr Cys
                50                  55                  60

Thr Gly Gly Thr Gly Gly Ala Ala Gly Cys Gly Cys Thr Gly Thr Ala
65                  70                  75                  80

Thr Cys Thr Gly Gly Thr Gly Thr Gly Cys Gly Gly Cys Gly Ala Ala
                85                  90                  95

Cys Gly Cys Gly Gly Cys Thr Thr Thr Thr Thr Thr Thr Ala Thr Ala
                100                 105                 110

Cys Cys Ala Ala Ala Cys Cys Gly Ala Thr Gly Cys Gly Cys Cys Gly
                115                 120                 125

Cys Gly Ala Ala Gly Cys Gly Ala Ala Gly Ala Thr Cys Thr Gly
                130                 135                 140

Cys Ala Gly Gly Thr Gly Gly Cys Cys Ala Gly Gly Thr Gly Gly
145                 150                 155                 160

Ala Ala Cys Thr Gly Gly Gly Cys Gly Gly Cys Gly Gly Cys Cys Cys
                165                 170                 175

Gly Gly Gly Cys Gly Cys Gly Gly Cys Ala Gly Cys Cys Thr Gly
                180                 185                 190

Cys Ala Gly Cys Cys Gly Cys Thr Gly Gly Cys Gly Cys Thr Gly Gly
                195                 200                 205

Ala Ala Gly Gly Cys Ala Gly Cys Cys Thr Gly Cys Ala Gly Gly Cys
    210                 215                 220

Gly Cys Gly Cys Gly Gly Cys Ala Thr Thr Gly Thr Gly Gly Ala Ala
225                 230                 235                 240

Cys Ala Gly Thr Gly Cys Thr Gly Cys Ala Cys Cys Ala Gly Cys Ala
                245                 250                 255

Thr Thr Thr Gly Cys Ala Gly Cys Cys Thr Gly Thr Ala Thr Cys Ala
                260                 265                 270

Gly Cys Thr Gly Gly Ala Ala Ala Ala Cys Thr Ala Thr Thr Gly Cys
                275                 280                 285

Gly Gly Cys
    290

<210> SEQ ID NO 10
<211> LENGTH: 97
<212> TYPE: PRT
<213> ORGANISM: Artificial Sequence
<220> FEATURE:
<223> OTHER INFORMATION: desB30 pro-insulin

<400> SEQUENCE: 10
```

```
Met Arg Gly Ser His His His His His His Arg Phe Val Asn Gln His
1               5                   10                  15

Leu Cys Gly Ser His Leu Val Glu Ala Leu Tyr Leu Val Cys Gly Glu
            20                  25                  30

Arg Gly Phe Phe Tyr Thr Lys Pro Met Arg Arg Glu Ala Glu Asp Leu
        35                  40                  45

Gln Val Gly Gln Val Glu Leu Gly Gly Pro Gly Ala Gly Ser Leu
50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys
                85                  90                  95

Gly

<210> SEQ ID NO 11
<211> LENGTH: 30
<212> TYPE: PRT
<213> ORGANISM: Artificial Sequence
<220> FEATURE:
<223> OTHER INFORMATION: B chain of DesB30MazideInsulin
<220> FEATURE:
<221> NAME/KEY: misc_feature
<222> LOCATION: (30)..(30)
<223> OTHER INFORMATION: Xaa can be any naturally occurring amino acid

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Xaa
            20                  25                  30

<210> SEQ ID NO 12
<211> LENGTH: 34
<212> TYPE: PRT
<213> ORGANISM: Artificial Sequence
<220> FEATURE:
<223> OTHER INFORMATION: APP
<220> FEATURE:
<221> NAME/KEY: MISC_FEATURE
<222> LOCATION: (1)..(1)
<223> OTHER INFORMATION: First glycine is L-homopropargylglycine (CAS
      98891-36-2)

<400> SEQUENCE: 12

Gly Glu Gly Glu Gly Glu Glu Lys Gly Glu Gly Glu Glu Lys Glu
1               5                   10                  15

Gly Glu Gly Glu Glu Lys Glu Gly Glu Glu Lys Gly Glu Gly
            20                  25                  30

Glu Glu

<210> SEQ ID NO 13
<211> LENGTH: 29
<212> TYPE: PRT
<213> ORGANISM: Homo sapiens

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

```
<210> SEQ ID NO 14
<211> LENGTH: 180
<212> TYPE: PRT
<213> ORGANISM: Homo sapiens

<400> SEQUENCE: 14
```

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
        180

```
<210> SEQ ID NO 15
<211> LENGTH: 31
<212> TYPE: PRT
<213> ORGANISM: Homo sapiens

<400> SEQUENCE: 15
```

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

```
<210> SEQ ID NO 16
<211> LENGTH: 38
<212> TYPE: PRT
<213> ORGANISM: Homo sapiens

<400> SEQUENCE: 16
```

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Asn His
        35

```
<210> SEQ ID NO 17
<211> LENGTH: 33
<212> TYPE: PRT
<213> ORGANISM: Homo sapiens
```

```
<400> SEQUENCE: 17

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 18
<211> LENGTH: 17
<212> TYPE: PRT
<213> ORGANISM: Homo sapiens

<400> SEQUENCE: 18

Thr Val Glu Gly Val Glu Ala Leu Lys Leu His Ile Leu Ala Ala Leu
1               5                   10                  15

Pro

<210> SEQ ID NO 19
<211> LENGTH: 9
<212> TYPE: PRT
<213> ORGANISM: Homo sapiens

<400> SEQUENCE: 19

Asp Ile Cys Leu Pro Arg Trp Gly Cys
1               5

<210> SEQ ID NO 20
<211> LENGTH: 6
<212> TYPE: PRT
<213> ORGANISM: Homo sapiens

<400> SEQUENCE: 20

Cys Val Glu Glu Ala Ser
1               5
```